United States Patent
Borch et al.

(10) Patent No.: US 8,324,378 B2
(45) Date of Patent: Dec. 4, 2012

(54) PRODRUGS AND CONJUGATES OF PRENYLATION INHIBITORS

(75) Inventors: Richard Frederic Borch, Lafayette, IN (US); Richard Anthony Gibbs, West Lafayette, IN (US); Michelle Martin Clark, Overland Park, KS (US); Farid Fouad, Youngstown, OH (US)

(73) Assignee: Purdue Research Foundation, West Lafayette, IN (US)

( * ) Notice: Subject to any disclaimer, the term of this patent is extended or adjusted under 35 U.S.C. 154(b) by 132 days.

(21) Appl. No.: 12/675,315

(22) PCT Filed: Aug. 29, 2008

(86) PCT No.: PCT/US2008/074870
§ 371 (c)(1),
(2), (4) Date: Feb. 25, 2010

(87) PCT Pub. No.: WO2009/029849
PCT Pub. Date: Mar. 5, 2009

(65) Prior Publication Data
US 2010/0249072 A1     Sep. 30, 2010

Related U.S. Application Data

(60) Provisional application No. 60/969,189, filed on Aug. 31, 2007.

(51) Int. Cl.
*C07D 345/00* (2006.01)
*C07D 517/00* (2006.01)

(52) U.S. Cl. ............... 540/1; 514/99; 549/218

(58) Field of Classification Search ............ None
See application file for complete search history.

(56) References Cited

U.S. PATENT DOCUMENTS

| 4,134,877 | A | 1/1979 | Morgan et al. |
| 5,233,031 | A | 8/1993 | Borch et al. |
| 2004/0121985 | A1 | 6/2004 | Gibbs et al. |

OTHER PUBLICATIONS

Gibbs et al Novel Farnesol and Geranylgeraniol analogues: A potential new class of anticancer agents directed against prenylation:, J. Med. Chem. 1999, 42, 3800-3808.*
Manne et al "Ras Farnesylation as a target for novel antitumor agents: potent and selective farnesyl diphosphate analogue inhibitors of farnesyltransferase", Drug Development Research, 34:121-137, 1995.*
Wu et al "Synthesis and biological activity of a N-2,3-dihydropropyl-N-chlorobutyl nucleoside phosphoramidate prodruges", Molecular Pharmaceutics, vol. 3, No. 4, 451-456, May 12, 2006.*
Meier et al "cyclosal-pro-nucleotides-Development of first and second generation chemical trojan horses for antiviral chemotherapy" Frontiers in Bioscience 9, 873-890, Jan. 1, 2004.*
International Serach Report Written Opinion for PCT/US2008/074870 completed Nov. 12, 2008.
International Search Report Written Opinion for PCT/US2008/074870 completed Dec. 11, 2008.
Ayllon, Veronica, et al., "Ras-induced Cellular Events (Review)", Mol. Mem. Biol., 2000, vol. 17, pp. 65-73.
Borch, Richard F., et al., "Synthesis and Evaluation of Nitroheterocyclic Phosphoramidates as Hypoxia-Selective Alkylating Agents", J. Med. Chem., 2000, vol. 43, pp. 2258-2268.
Diem, K., et al., "Scientific Tables", 7th Ed., 1970, Geigy Pharmaceuticals, Ardley, New York, pp. 537-538.
Freireich, Emil J., et al., "Quantitative Comparison of Toxicity of Anticancer Agents in Mouse, Rat, Hamster, Dog, Monkey, and Man", Cancer Chemother. Rep., 1966, vol. 50, No. 4, pp. 219-231.
Gibbs, Barbara S., et al., "Novel Farnesol and Geranygeraniol Analogues: A Potential New Class of Anticancer Agents Directed Against Protein Prenylation", J. Med. Chem., 1999, vol. 42, pp. 3800-3808.
Gibbs, Richard A., et al., "Non-Peptidic Prenyltransferase Inhibitors: Diverse Structural Classes and Surprising Anti-Cancer Mechanisms", Curr. Med. Chem., 2001, vol. 8, pp. 1437-1465.
Hurwitz, Herbert I., et al., "Prenylation of CaaX-Type Proteins: Basic Principles Through Clinical Applications", Curr. Top. Membr., 2002, vol. 52, pp. 531-550.
Jackson, Janis H., et al., "Farnesol Modification of Kirsten-ras Exon 4B Protein is Essential for Transformation", Proc. Natl. Acad. Sci., 1990, No. vol. 87, pp. 3042-3046.
Meyers, Caren L. Freel, et al., "Synthesis and Biological Activity of Novel 5-Fluoro-2'-Deoxyuridine Phosphoramidate Prodrugs", J. Med. Chem., 2000, vol. 43, pp. 4313-4318.
Mu, YongQi, et al., "Cuprate-Mediated Synthesis and Biological Evaluation of Cyclopropyl- and tert-Butylfarnesyl Diphosphate Analogs", J. Org. Chem., 1996, vol. 61, pp. 8010-8015.
Mu, YongQi, et al., "Coupling of Isoprenoid Triflates with Organoboron Nucleophiles: Synthesis and Biological Evaluation of Geranylgeranyl Diphosphate Analogues", Bioorg. Med. Chem., 2002, vol. 10, pp. 1207-1219.
Xie, Haibo, et al., "Synthesis and Biological Evaluation of the Geometric Farnesylated Analogues of the a-Factor Mating Peptide of *Saccharomyces cerevisiae*", J. Org. Chem., 2000, vol. 65, pp. 8552-8563.
Zhou, Chunmei, et al., "Aromatic Farnesyl Diphosphate Analogues: Vinyl Triflate-Mediated Synthesis and Preliminary Enzymatic Evaluation", Bioorg. Med. Chem. Lett., 2002, vol. 12, pp. 1417-1420.

* cited by examiner

*Primary Examiner* — Brandon Fetterolf
*Assistant Examiner* — Jean Cornet
(74) *Attorney, Agent, or Firm* — Barnes & Thornburg LLP

(57) ABSTRACT

Described herein are neutral prodrugs of phosphorus-containing inhibitors of farnesyl transferase that include one or more phosphate fragments or analogs of phosphate fragments. Analogs of phosphate fragments include various linkers other than oxygen connecting the phosphate fragment to the remaining portion of the drug, such as but not limited to linkers forming phosphoramidates, phosphonates, difluorophosphonates, phosphordiamidates, and the like.

2 Claims, No Drawings

PRODRUGS AND CONJUGATES OF PRENYLATION INHIBITORS

CROSS REFERENCE TO RELATED APPLICATIONS

This application is a U.S. national counterpart application, under 35 U.S.C. §3.71(c), of international application serial No. PCT/2008/074870 filed Aug. 29, 2008, which claims the benefit of U.S. Provisional Patent Application Ser. No. 60/969,189 filed on Aug. 31, 2007, the entire disclosures of which are each hereby incorporated by reference.

FIELD OF INVENTION

This invention relates to intracellular delivery of phosphate-substituted therapeutic compounds and analogs thereof. More particularly, this invention relates to prodrugs of phosphorus-containing inhibitors of farnesyl transferase, and prodrugs of drug-phosphate conjugates and analogs of drug-phosphate conjugates.

BACKGROUND

Prenylation, the introduction of a farnesyl or geranylgeranyl moiety onto the sulfhydryl group of certain proteins, is an important post-translational modification central to many cellular processes. The enzymes responsible for these prenylations include the protein farnesyltransferase (FTase) and geranylgeranyltransferase (GGTase). Prenylation may be required to give a protein sufficient hydrophobicity for translocation to the plasma membrane. Many proteins that undergo prenylation are critical to signal transduction pathways, and therefore cell membrane localization is essential for these proteins to operate properly (see, for example, Hurwitz, H. I.; Casey, P. J. Prenylation of CaaX-type proteins: Basic principles through clinical applications, in *Curr. Top. Membr.* 2002, 52, 531-550; and Gibbs, R. A.; Zahn, T. J.; Sebolt-Leopold, J. S. Non-peptidic prenyltransferase inhibitors: Diverse structural classes and surprising anti-cancer mechanisms, in *Curr. Med. Chem.* 2001, 8, 1437-1465).

One such signal transduction protein that requires farnesylation in order to function properly is Ras (see, Jackson, J. H.; Cochrane, C. G.; Bourne, J. R.; Solski, P. A.; Buss, J. E.; Der, C. J. Farnesol modification of kirsten-ras exon 4B protein is essential for transformation, in *Proc. Natl. Acad. Sci.* 1990, 87, 3042-3046). Because mutated Ras proteins that are constitutively activated are seen in a significant number of cancers, there is a great deal of interest in preventing Ras membrane localization. One way to prevent Ras membrane localization is to inhibit FTase, the enzyme responsible for farnesylating Ras (see, for example, Ayllon, V.; Rebollo, A. Ras-induced Cellular Events (Review), in *Mol. Mem. Biol.* 2000, 17, 65-73). Significant research efforts have been directed towards developing FTase inhibitors that mimic farnesyl pyrophosphate, which is the natural substrate for the enzyme (see, Gibbs, R. A.; Zahn, T. J.; Sebolt-Leopold, J. S. Non-peptidic prenyltransferase inhibitors: Diverse structural classes and surprising anti-cancer mechanisms, in *Curr. Med. Chem.* 2001, 8, 1437-1465). Indeed, the pyrophosphates of 3-allylfarnesol and 3-t-butylfarnesol have been shown to be nanomolar inhibitors of FTase, and the pyrophosphate of 3-(3,3-dimethylallyl)farnesol is a novel protein-selective inhibitor of this enzyme. These phosphate-substituted compounds are highly charged, however, and it is unlikely that they will be capable of traversing the cell membrane and entering the cell.

It has been discovered that the intracellular delivery of monophosphate analogs of such inhibitors may provide an effective therapeutic approach to treating diseases that are responsive to the inhibition of prenylation.

SUMMARY OF INVENTION

Described herein are compounds and methods that are useful for the intracellular delivery of polar phosphates, and analogs and derivatives thereof, of prenyl groups, and analogs and derivatives thereof. It is appreciated that such phosphates of prenyl groups, and analogs and derivatives thereof, are themselves inhibitors of prenylation, such as inhibitors of FTase, and may also serve as substrates for phosphorylation, being converted to pyrophosphates, and analogs and derivatives thereof. Such pyrophosphates, and analogs and derivatives thereof, may also be inhibitors of prenylation, such as inhibitors of FTase.

The invention described herein includes neutral prodrugs of phosphorus-containing inhibitors of farnesyl transferase that include one or more phosphate fragments or analogs of phosphate fragments. Analogs of phosphate fragments include various linkers other than oxygen connecting the phosphate fragment to the remaining portion of the drug, such as but not limited to linkers forming phosphoramidates, phosphonates, difluorophosphonates, oxophosphonates, thiophosphonates, and the like. Without being bound to theory, the neutral prodrug is believed to enter the cell by passive diffusion, and then intracellular activation of the prodrug generates an intermediate that spontaneously releases the corresponding phosphate-containing drug, or analog thereof, within the cell. The invention described herein is also directed to drugs that are phosphorylated after delivery. It is appreciated that those drugs that are phosphorylated after delivery may only become active as drugs following phosphorylation. The invention described herein is also directed to analogs of drugs that are phosphorylated after delivery, including phosphonate analogs that may be phosphorylated to the pyrophosphate analog. Analogs of drugs that are phosphorylated after delivery include phosphorylated drugs where the linker connecting the phosphate fragment to the drug fragment is other than oxygen, such as, but not limited to linkers forming phosphoramidates, phosphonates, difluorophosphonates, oxophosphonates, thiophosphonates, and the like.

As used herein, prenyl groups are mono-olefins, polyolefins, mono or polyalkynes, and alkenylalkynes comprising at least one 3-methyl-but-2-ene-1,4-diyl unit, or an analog or derivative thereof. Illustrative examples of prenyl groups are farnesol, geraniol, farnesylfarnesol, farnesylgeraniol, geranylgeraniol, including a wide variety of farnesol and geraniol analogs, and the like. It is to be understood that prenyl groups also include a wide variety of optional branching groups on the olefin, alkynyl, or alkenylalkynyl core structure. Illustratively, additional examples of prenyl groups include 3-t-butylfarnesol, 3-allylfarnesol, 3-(3-methyl-but-2-en-1-yl)-5-(4-phenyl)phenylpent-2-en-1-ol, and 3-(but-3-en-1-yl)-7,11-dimethyldodeca-2E,6E,10-trien-1-ol, and the like. It is to be understood that the foregoing illustrative prenyl groups may be linked together and included in the drugs described herein.

In another embodiment, prodrugs of prenyl groups are described, including but not limited to, prodrugs of 3-t-butylfarnesol, 3-allylfarnesol, and geranylgeraniol. Such prodrugs of prenyl groups are prepared as described herein, and also using convention organic synthetic methods, which may be correspondingly adapted and optimized. In another illustrative embodiment, the prodrugs described herein are formed from drugs, including farnesol monophosphate analogs, that are phosphorylated in vivo after delivery or administration to a patient. In one aspect, the drug is more active, or activated only, after phosphorylation by a biological pathway present in the patient.

In another illustrative embodiment, the prodrugs described herein are resistant to phosphatases, including intracellular phosphatases that may cleave the phosphorus-containing fragment from the prodrug conjugate or conjugate after the prodrug is converted into the phosphorus-containing drug or drug-conjugate analog. As stated herein, the efficacy of many drugs are aided by or dependent upon phosphorylation. Thus, prodrugs described herein include embodiments that are resistant to metabolic degradation and therefore have increased half-lives in the patient being treated. It is appreciated that in certain disease states and/or for certain patients, phosphatases may be particularly abundant and their presence may hamper treatment efforts using compounds that are susceptible to phosphatase degradation. In particular, in one variation, the prodrugs described herein are formed from drugs, including farnesol monophosphate analogs, that are resistant to degradation by phosphatases or other enzymes that cleave phosphorus-oxygen bonds, including nucleotidases, endonucleases, exonucleases, and the like. It is understood herein that such degradation resistance may be accomplished by the replacement of the oxygen atom linker that connects the phosphorus fragment with the rest of the drug or drug-phosphate conjugate with a sulfur atom, an optionally substituted nitrogen atom, and/or with one or more carbon atoms, each of which may be substituted, such as with hydrogen, alkyl, and fluoro substituents, and the like, alone or in combination. It is also appreciated that in the embodiments described herein, complete phosphatase resistance may not be achieved, and therefore certain phosphatases may degrade the drug-phosphoester conjugate, while others may not. It is therefore further appreciated that in such variations of the methods described herein that include prodrugs susceptible to selective phosphatase activity, such partial or selective phosphatase resistance may be advantageous.

In another illustrative embodiment, a compound of formula

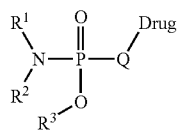

or a pharmaceutically acceptable salt derivative thereof, is described, where $R^1$ is —$(CR_2)_nY$; n is an integer from 2 to about 5; $R^2$ is —$(CR_2)_mX$; m is an integer from 2 to about 5; where R is in each instance an independently selected substituent, including hydrogen, alkyl, fluoro, and the like; or any geminal pair of such groups R can be taken together with the attached carbon to form a ring, including a carbocyclic ring, or heterocyclic ring; X is a nucleophilically labile group, including halo, alkoxy, phenoxy, acyloxy, sulfonyloxy, and the like; Y is a polar group, including COOH or a salt thereof, $SO_3H$ or a salt thereof, $PO_3H_2$ or a salt thereof, and the like; $R^3$ is a biologically labile ester forming group; Q is a bond or a linker selected from O, $NR^4$, $CR^9R^{10}$, or $CF_2$; wherein $R^4$ is hydrogen, alkyl, or acyl; $R^9$ and $R^{10}$ are independently selected from the group consisting of hydrogen, alkyl, haloalkyl, alkoxyl, and fluoro; or $R^9$ and $R^{10}$ along with the attached carbon form an optionally substituted ring; and Drug is a prenyl group, it being understood that such prenyl groups include analogs and derivatives, as described herein.

In another illustrative embodiment, a compound of formula

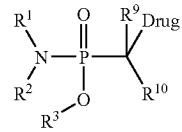

or a pharmaceutically acceptable salt derivative thereof, is described, where $R^1$, $R^2$, and $R^3$ are as described herein; $R^9$ and $R^{10}$ are independently selected from the group consisting of hydrogen, alkyl, haloalkyl, alkoxyl, and fluoro; or $R^9$ and $R^{10}$ along with the attached carbon form an optionally substituted ring; and Drug is a prenyl group, it being understood that prenyl groups include analogs and derivatives, as described herein.

In another illustrative embodiment, a compound of formula

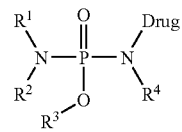

or a pharmaceutically acceptable salt derivative thereof, is described, where $R^1$, $R^2$, and $R^3$ are as described herein; $R^4$ is hydrogen, alkyl, acyl, and the like; and Drug is a prenyl group, it being understood that prenyl groups include analogs and derivatives, as described herein. It is appreciated that in this embodiment, complete phosphatase resistance may not be desirable, and that selective phosphatase resistance may be achieved by suitable selection of the $R^4$ group, where certain phosphatases may degrade the drug-phosphoramidate conjugate while others may not.

In another illustrative embodiment, a compound of formula

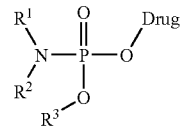

or a pharmaceutically acceptable salt derivative thereof, is described, where $R^1$ is —$(CR_2)_nY$; n is an integer from 2 to about 5; $R^2$ is —$(CR_2)_mX$; m is an integer from 2 to about 5; R is in each instance an independently selected substituent, including hydrogen, alkyl, fluoro, and the like; or any geminal pair of such groups R can be taken together with the attached carbon to form a ring, including a carbocyclic ring, or heterocyclic ring; X is a nucleophilically labile group, including halo, alkoxy, phenoxy, acyloxy, sulfonyloxy, and the like; Y is a polar group, including COOH or a salt thereof, $SO_3H$ or a salt thereof, $PO_3H_2$ or a salt thereof, and the like; $R^3$ is a biologically labile ester forming group; and Drug is a prenyl group, it being understood that prenyl groups include analogs and derivatives, as described herein.

In another illustrative embodiment, a compound of formula

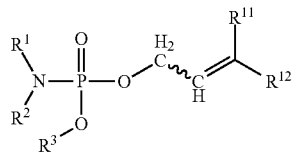

or a pharmaceutically acceptable salt derivative thereof, is described, where $R^1$ is —$(CR_2)_nY$; n is an integer from 2 to about 5; $R^2$ is —$(CR_2)_mX$; m is an integer from 2 to about 5; R is in each instance an independently selected substituent, including hydrogen, alkyl, fluoro, and the like; or any geminal pair of such groups R can be taken together with the attached carbon to form a ring, including both carbocyclic rings and heterocyclic rings; X is a nucleophilically labile group, including halo, alkoxy, phenoxy, acyloxy, sulfonyloxy, and the like; Y is a polar group, including COOH or a salt thereof, $SO_3H$ or a salt thereof, $PO_3H_2$ or a salt thereof, and the like; $R^3$ is a biologically labile ester forming group; wherein $R^{11}$ is alkyl, haloalkyl, alkenyl, haloalkenyl, alkynyl, aryl, heteroaryl, or arylalkyl; $R^{12}$ is alkyl, alkenyl, cycloalkyl, arylalkyl, arylalkenyl, heteroarylalkyl, heteroarylalkenyl, or $CH_2CH_2CH=CR^{13}(CH_2CH_2CH=C(CH_3))_p$, wherein p is 1, 2, or 3; and $R^{13}$ is alkyl, alkenyl, haloalkyl, haloalkenyl, or halide.

In another illustrative embodiment, a compound of formula

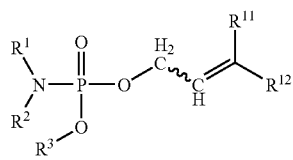

or a pharmaceutically acceptable salt derivative thereof, is described, where $R^1$ is 4-carboxybutyl; $R^2$ is 4-chlorobutyl; $R^{32}$—(5-nitrofuryl)methoxy; $R^{11}$ is alkyl, haloalkyl, alkenyl, haloalkenyl, alkynyl, aryl, heteroaryl, or arylalkyl; $R^{12}$ is alkyl, alkenyl, cycloalkyl, arylalkyl, arylalkenyl, heteroarylalkyl, heteroarylalkenyl, or $CH_2CH_2CH=CR^{13}(CH_2CH_2CH=C(CH_3))_p$, where p is 1, 2, or 3; and $R^{13}$ is alkyl, alkenyl, haloalkyl, haloalkenyl, or halide.

It is appreciated that in any prodrug described herein, prenyl groups or analogs thereof may be modified as is necessary to provide a derivative where a suitable linking atom or atoms allow for conjugation with the phosphorus-containing portion of the prodrug conjugate. For example, in addition to direct oxygen-mediated attachment of a prenyl moiety or analogs thereof to the phosphorus-containing portion of a prodrug, the phosphorus-containing portion may be attached to a prenyl moiety or analogs thereof through a linker, such as methylene, difluoromethylene, carbonyl, and the like. Alternatively, farnesol or analogs thereof may be derivatized with for example a suitable heteroatom, such as thio or optionally substituted amino, and the prenyl moiety or analogs thereof then attached directly to the phosphorus-containing portion via the heteroatom or through an optional linker. In the case of an optionally substituted amino, that nitrogen may be directly attached to the phosphorus to form a prodrug including a phosphordiamidate.

In one aspect, the drugs described herein include a phosphonate linkage between the phosphorus and the farnesol analogs or derivatives thereof. In another aspect, the prodrugs described herein include a difluorophosphonate linkage between the phosphorus and the farnesol analogs or derivatives thereof. In yet another aspect, the prodrugs described herein include a phosphoester linkage between the phosphorus and farnesol or analogs thereof. In still another aspect, the prodrugs described herein include a phosphoramidate linkage between the phosphorous and the farnesol analogs or derivatives thereof.

Illustrative examples of the compounds described herein, and also illustrating the group Q, that are ultimately delivered to the cell following removal of the masking and delivery groups include

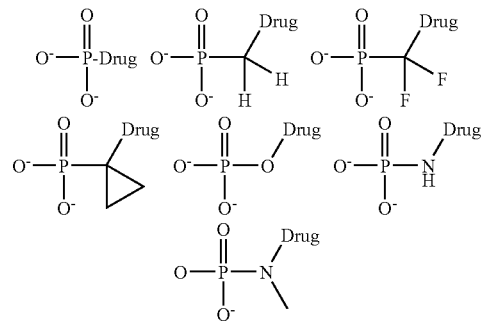

where Drug is as described herein.

DETAILED DESCRIPTION

One general strategy for the intracellular delivery of phosphate-containing compounds utilized in the present invention is outlined in Scheme 1.

Scheme 1

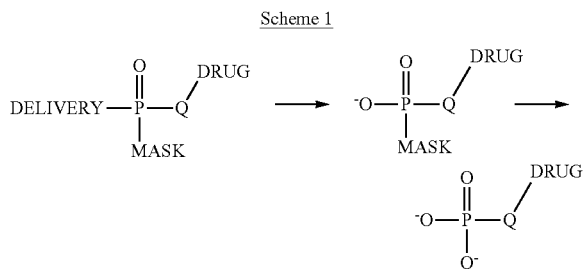

In Scheme 1, Delivery is a delivery group, Mask is a masking group, Drug is the drug or drug fragment, and Q is an optional linker forming the conjugate. Briefly, the phosphate-substituted compound to be delivered intracellularly is synthesized to include a delivery group and a masking group. In one embodiment, the masking group is illustratively a (substituted alkyl)amine or bis(substituted alkyl)amine moiety that may be modified intracellularly. In one aspect, modification of the masking group occurs while retaining the delivery group. In another aspect, the delivery group is removed before modification of the masking group occurs. In another aspect, the masking group undergoes intramolecular cyclization and subsequent cleavage by hydrolysis. In another aspect, intramolecular cyclization occurs contemporaneously, or even simultaneously in a concerted or anchimerically-assisted process, with hydrolysis of the masking group. The masking group is generally stable as long as the delivery group remains attached to the phosphorus atom. The delivery group is generally a group that is subject to intracellular hydrolysis, such as a biologically labile ester-forming group, or an ester that is readily hydrolyzed intracellularly. Illustratively, the delivery group includes nitrofuryl groups, perhydrooxazines, and the like.

In one illustrative embodiment, a mechanism of prodrug release of drug-phosphate, optionally substituted drug-phosphoramidate, or optionally substituted drug-phosphonate conjugates described herein is outlined in Scheme 2

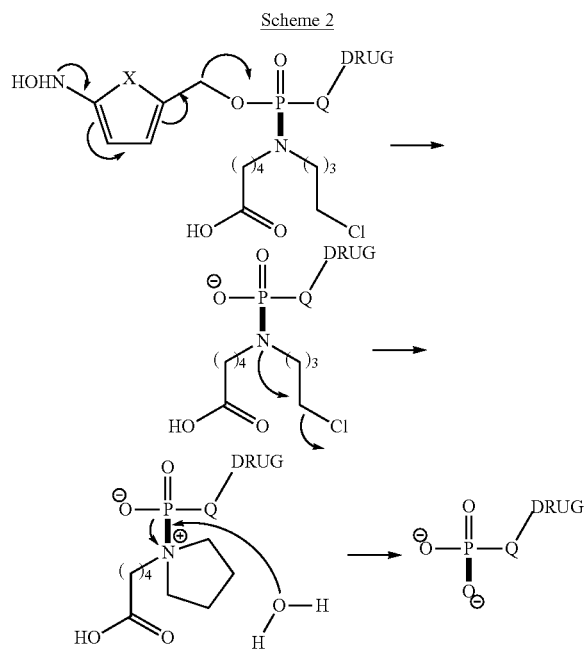

where the delivery group is illustratively a nitrofurylmethyloxy group (X═O) that has been bioreduced, and the masking group is illustratively a chlorobutyl(carboxybutyl)amine. Upon intracellular activation of the delivery group by bioreduction, and subsequent removal, the masking group undergoes intramolecular cyclization and P—N bond cleavage (i.e., spontaneous or via hydrolysis) in the intracellular environment, thus releasing the desired phosphate-containing compound. It is appreciated that the sequence of steps leading to release of the drug or drug-conjugate free of both the masking and delivery groups may occur in a different order. For example, removal of the delivery group may precede any intracellular modification of the masking group, as shown in Scheme 2. Alternatively, cyclization of the masking group may be followed by immediate P—N bond cleavage prior to removal of the delivery group. It is to be understood that further variation of the mechanisms of release of the drug or drug-conjugate are contemplated.

The formation of prodrugs of each of these drugs, drug-phosphate conjugates, and phosphate analogs thereof may enhance their efficacy and specificity. In one embodiment, prodrugs of drugs that include a phosphate fragment or phosphate fragment analog are described. In another embodiment, prodrugs of drugs that are phosphorylated after delivery are described. In this latter embodiment of prodrugs of drugs that are phosphorylated after delivery, the prodrugs may be derived from phosphorylated versions of the drug and/or from analogs of phosphorylated versions of the drug, including but not limited to phosphoramidates, phosphonates, difluorophosphonates, oxophosphonates, thiophosphonates, and the like. Also in this latter embodiment of prodrugs of drugs that are phosphorylated after delivery, "delivery" is to be understood to include any in vitro, in vivo, or other in situ situation where the drug is introduced to a condition or set of conditions under which it is phosphorylated. As used throughout, the term "drug" will refer both to compounds that include a phosphate fragment or phosphate fragment analog, as well as to compounds that are phosphorylated after delivery. For example, the term "drug" as used herein when referring to certain FTase inhibitors accordingly includes farnesol monophosphate analogs, i.e., those that include farnesol or analogs thereof and a phosphate fragment or analog thereof, and to farnesol monophosphate analogs that are phosphorylated after delivery. It will be understood by the context in which the term "drug" is used whether the term is intended to apply to drugs already including a phosphate fragment or to drug-phosphate conjugates. It is also to be understood that the term "drug" includes derivatives of farnesol that may be prepared to include additional atoms or functional groups that are used for attaching the phosphorous-containing portion of the prodrug. Such additional atoms or functional groups may be referred to as linkers.

In one aspect, the (substituted alkyl)amine or bis(substituted alkyl)amine is a substituted ethylamine or bis(substituted ethyl)amine, such as a ethyl substituted with a leaving group including halo, alkoxy, acyloxy, sulfonyloxy, and the like. The leaving group is understood to be any electrophilic group capable of being nucleophilically displaced from the carbon atom to which it is bound intermolecularly or intramolecularly. It is appreciated that such nucleophilic lability can be exploited in a controlled fashion to facilitate the unmasking of the prodrug and ultimate release of the drug phosphate conjugate or analog thereof. It is further appreciated that the substituted ethylamine or bis(substituted ethyl)amine, including the haloethylamine or bis(haloethyl)amine derivatives, may also be irreversible inhibitors leading to irreversible adducts such as formation of cross-linked structures with nucleic acids like DNA and RNA, enzymes, and the like. In another aspect, the (substituted alkyl)amine or bis(substituted alkyl)amine includes a longer chain (substituted alkyl)amine, such as a substituted butyl and/or substituted pentyl group. In this aspect, the inhibitors may be reversible inhibitors. Similarly, the substitutions include leaving groups such as halo, alkoxy, acyloxy, sulfonyloxy, and the like. It is appreciated that in each of the illustrative examples the alkyl may have branching substituents, including additional alkyl groups, spiro-ring fusions, and the like. In one illustrative aspect, such branching substituents are not leaving groups.

It is appreciated that the efficacy of a drug lacking any of the delivery and masking groups described herein may be hampered by the dependence on an additional endogenous functionalization pathway. Further, in some disease states, the necessary pathway is compromised, further minimizing the efficacy of the drug. In some aspects, the prodrugs described herein include the necessary or desirable phosphorus-containing fragment at dosing to the patient being treated, and therefore do not require additional in vivo modification or activation. In additional aspects, the prodrugs described herein are illustratively prepared to mask the negative charge, or double negative charge of the phosphorus-containing fragment. It is appreciated that highly charged molecules often suffer from poor absorption and/or transport to the relevant tissues of cells that are the object of treatment.

With regard to illustrative formulae:

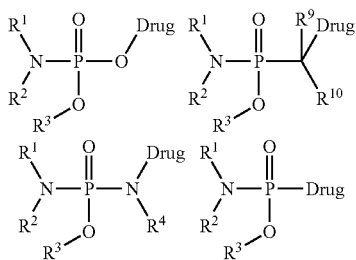

and pharmaceutically acceptable salt derivatives thereof, where $R^1$, $R^2$, $R^3$, $R^4$, $R^9$, $R^{10}$, and Drug are as defined herein, the electrophilic group X, which is included in $R^2$, is illustratively halo, such as chloro, bromo, or iodo. However, it is appreciated that the nature of that group may be varied provided that it can serve as a leaving group to enable activation and/or cyclization and concomitant quaternization of the phosphorous-bound nitrogen atom in vivo following administration of the phosphoramidate prodrugs to a patient. Other electrophilic leaving groups such as acetoxy, haloacetoxy, alkyl and arylsulfonyloxy, each of which may be optionally substituted, such as methane sulfonyloxy, trifluoromethanesulfonyloxy, tosyloxy, brosyloxy, nosyloxy, and the like may also be used. Further, with regard to the above illustrative formulae, the polar group Y, which is included in $R^1$, is illustratively COOH or a salt thereof, $SO_3H$ or a salt thereof, or $PO_3H_2$ or a salt thereof. However, it is appreciated that the nature of that group may be varied provided that it can serve to increase the hydrophilicity of the phosphoramidate prodrugs.

The term "biologically labile ester forming group," as used herein to describe $R^3$, refers to those ester forming groups derived from alcohols that form ester derivatives that are stable under drug manufacture and storage conditions but are subject to hydrolysis when exposed to biological conditions in vivo. Illustratively, the ester forming groups used herein exhibit minimal susceptibility to hydrolysis in the body fluids in the extracellular space but exhibit susceptibility to hydrolysis in the intracellular space illustratively where ester-degrading reductive conditions are prominent. Thus, in one embodiment, the biologically labile ester forming group on the prodrugs described herein are those ester forming groups that are susceptible to hydrolysis under mild reductive conditions, including, but not limited to, nitroaryl, including nitrofuryl, nitrothienyl, nitropyrroyl, nitroimidazoyl, and nitroarylalkyl, and the like, indanyl, napthoquinolyl, perhydrooxazinyl, and the like. The nature of the ester forming group $R^3$ is not critical provided that the group exhibits susceptibility to hydrolysis under intracellular conditions, such as biological conditions that exhibit reductive potential.

In one illustrative aspect of the embodiments described herein, $R^1$ is 4-carboxybutyl, i.e., Y in the above formulae is COOH, R is hydrogen, and the integer n is 4. In another illustrative aspect, $R^2$ is $—(CF_2)_mX$, and the integer m is 4 or 5. In another illustrative aspect, each R is hydrogen. In another illustrative aspect, X is halogen, such as chloro. In another illustrative aspect, both $R^9$ and $R^{10}$ are hydrogen or both $R^9$ and $R^{10}$ are fluoro. In another illustrative aspect, $R^3$ is heteroarylalkyloxy, optionally substituted with an electron withdrawing group, such as nitro, alkylsulfonyl, cyano, halo, and the like. In another illustrative aspect, $R^3$ is optionally substituted arylalkyloxy, such as optionally substituted benzyloxy. In another illustrative aspect, $R^3$ is optionally substituted 1,3-heterocycloalkyloxy, such as an optionally substituted tetrahydro-1,3-oxazine alkyloxy. It is appreciated that each of these illustrative aspects may be included in the various embodiments described herein alone or in combination with other aspects.

In one aspect where $R^3$ is optionally substituted 1,3-heterocycloalkyloxy, $R^3$ is [2-(4,4,6-trimethyltetrahydro-1,3-oxazin-2-yl)ethyl]oxy. Prodrugs that include $R^3$ as [2-(4,4,6-trimethyltetrahydro-1,3-oxazin-2-yl)ethyl]oxy may be prepared by conventional methods. Illustratively, and as described by Borch et al. in U.S. Pat. No. 5,233,031 the synthetic methods of which are incorporated herein by reference, heating a [2-(2,2-dimethyl-1,3-dioxalane-4-yl)ethyl]oxy-containing phosphoramidate in 80% aqueous acetic acid at 80° C. for 30 minutes, with subsequent neutralization with NaOH affords the corresponding vicinal diol. Subsequent oxidation of the vicinal diol, with $NaIO_4$ in THF containing pH 5 acetate buffer, to the corresponding aldehyde followed by treatment with 4-methyl-4-amino-2-pentanol in $CH_2Cl_2$ over molecular sieves yields $R^3$ as [2-(4,4,6-trimethyltetrahydro-1,3-oxazin-2-yl)ethyl]oxy. In another aspect where $R^3$ is optionally substituted heteroarylalkyloxy, $R^3$ is nitrofurylmethyloxy. Prodrugs described herein include $R^3$ as nitrofurylmethyloxy. It is appreciated that each of these illustrative aspects may be included in the various embodiments described herein alone or in combination with other aspects.

The prodrugs described herein may be prepared to increase cell permeability of the drug or drug-phosphate conjugate or analog thereof, by selective activation. In the illustrative aspect where $R^3$ is optionally substituted heteroarylalkyloxy, one variation includes nitrofurylmethyloxy. It is appreciated that the prodrug activation may be initiated by bioreductive elimination of the delivery group followed by spontaneous liberation of the masking group, as generally described by Meyers, C. L. F.; Hong, L.; Joswig, C.; and Borch, R. F. in J. Med. Chem. 2000, 43:4313-4318, the disclosure of which is incorporated herein by reference. The presence of a reducing environment in solid tumors has been established by Borch, R. F.; Liu, J.; Schmidt, J. P.; Marakovits, J. T.; Joswig, C.; Gipp, J. J.; Mulcahy, R. T. in J. Med. Chem. 2000, 43:2258-2268, the disclosure of which is incorporated herein by reference, which allows a bioreductive activation prodrug strategy to achieve selectivity in tumor cells, as described herein.

The compounds that can be utilized as described herein to form prodrugs include a prenyl group, or analogs or derivatives thereof, farnesol, and analogs of farnesol and derivatives thereof, that can exhibit biological activity as their corresponding phosphates, or, alternatively, their phosphonate analogs, or phosphoramidate analogs. It is understood that for drugs that already include a phosphate radical or analog thereof, such as farnesol monophosphate, the drug fragment excluding the phosphate radical or analog thereof is used as described herein in preparing prodrugs. Illustratively, drug fragments that are converted to prodrugs as described herein are 3-t-butylfarnesol, 3-allylfarnesol, and geranylgeraniol, and other farnesol analogs where the hydrocarbon portion may be represented as

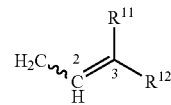

wherein R$^{11}$ is alkyl, haloalkyl, alkenyl, haloalkenyl, or alkynyl; and R$^{12}$ is CH$_2$CH$_2$CH=CR$^{13}$(CH$_2$CH$_2$CH=C(CH$_3$))$_p$, wherein p is 1 or 2; and R$^{13}$ is methyl (R$^a$).

Also described herein are prodrugs formed from drug fragments that include farnesol, farnesol analogs, and derivatives thereof, the hydrocarbon portion of which can be represented as

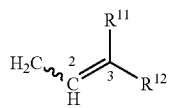

wherein R$^{11}$ is alkyl, haloalkyl, alkenyl, haloalkenyl, or alkynyl; and R$^{12}$ is CH$_2$CH$_2$CH=CR$^{13}$(CH$_2$CH$_2$CH=C(CH$_3$))$_p$, wherein p is 1 or 2, and R$^{13}$ is alkyl, haloalkyl, alkenyl, haloalkenyl, or alkynyl (R$^b$); or as

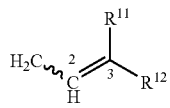

wherein R$^{11}$ is alkyl, haloalkyl, alkenyl, haloalkenyl, alkynyl, aryl, heteroaryl, or arylalkyl; and R$^{12}$ is C$_4$-C$_{15}$ alkyl (R$^c$); or as

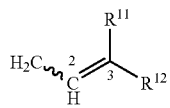

R$^{11}$ is alkyl, haloalkyl, alkenyl, haloalkenyl, or alkynyl; R$^{12}$ is CH$_2$CH$_2$R$^{14}$, where R$^{14}$ is selected from the group consisting of cyclohexyl, phenyl, aryl, heteroaryl, naphthyl, biphenyl, biaryl and bi-heteroaryl; each of which is optionally substituted (R$^d$); or as

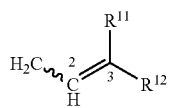

R$^{11}$ is alkyl, haloalkyl, alkenyl, haloalkenyl, or alkynyl; and R$^{12}$ is CH$_2$CH$_2$CH=CR$^{13}$(CH$_2$CH$_2$CH=C(CH$_3$))$_p$, wherein p is 1, 2 or 3; and R$^{13}$ is alkyl, haloalkyl, alkenyl, haloalkenyl, or alkynyl (R$^e$); or as

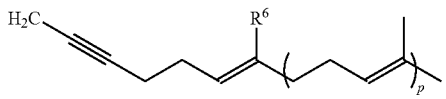

wherein R$^{12}$ is alkyl, alkenyl, cycloalkyl, arylalkyl, arylalkenyl, heteroarylalkyl, heteroarylalkenyl, or CH$_2$CH$_2$CH=CR$^{13}$(CH$_2$CH$_2$CH=C(CH$_3$))$_p$, wherein p is 1, 2, or 3; and R$^{13}$ is alkyl, alkenyl, haloalkyl, haloalkenyl, or halide (R$^f$). In general, it is to be understood that any farnesol analog or derivative thereof may be utilized to prepare a prodrug, a drug-phosphate conjugate or analog thereof, and/or a prodrug of a drug-phosphate conjugate or analog thereof as described herein. In each of the formulae R$^a$, R$^b$, R$^c$, R$^d$, R$^e$, and R$^f$, it is appreciated that other geometrical isomers, or combinations of geometrical isomers, about the double bonds may also be drugs or drug fragments from which prodrugs are formed as described herein. In an illustrative aspect, and referring to R$^b$, the double bond between carbon atoms 2 and 3 has a trans configuration when the double bond between carbons atoms 6 and 7 has a cis configuration, and has a cis configuration when the double bond between carbon atoms 6 and 7 has a trans configuration.

In another illustrative embodiment where the drug is a farnesol monophosphate analog, including, but not limited to, 3-t-butylfarnesol monophosphate or 3-allylfarnesol monophosphate, or a geranylgeranyl monophosphate analog, the prodrug is a phosphoramidate compound of general formula (I):

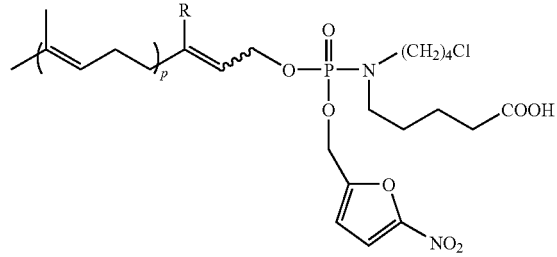

(I)

or a pharmaceutically acceptable salt derivative thereof, wherein R is tent-butyl (as in Compound 8), allyl (as in Compound 11), and methyl (as in Compound 14), respectively, and p is 1, 2, or 3.

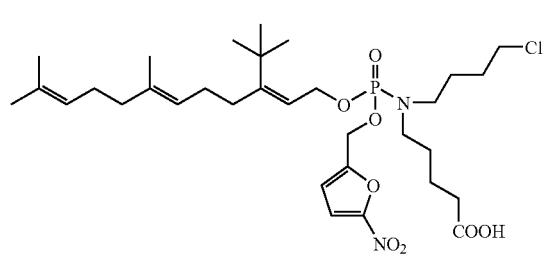

8

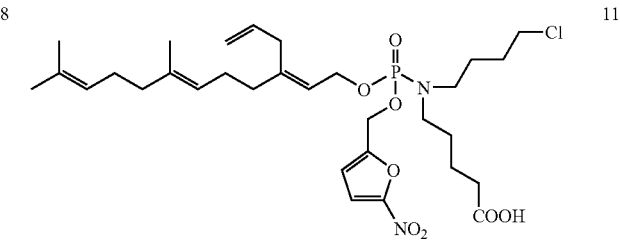

11

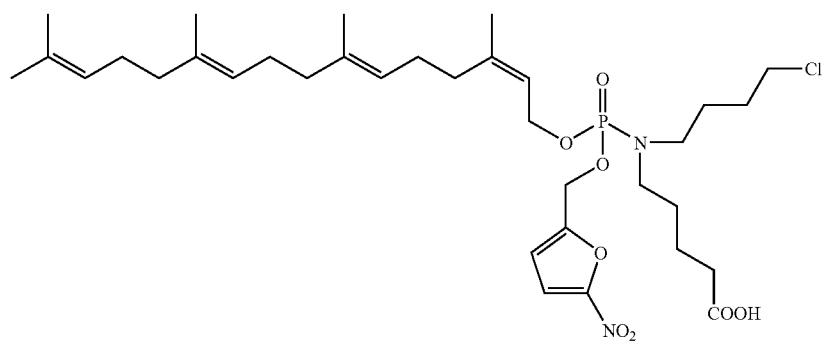

Further, analogs of the prodrugs of formula I are contemplated based on farnesol analogs and derivatives thereof, the hydrocarbon portion of which is as set forth above for $R^a$, $R^b$, $R^c$, $R^d$, $R^e$, and $R^f$. It is appreciated that in each of these illustrative embodiments, one or more chiral centers may be included, and that both possible optical isomers at each chiral center are contemplated to be included in the invention described herein. Further, it is also to be understood that various mixtures, including racemic mixtures, or other diastereomeric mixtures of the various optical isomers may be used in one or more embodiments described herein. It is further appreciated that various geometric isomers may be used in one or more embodiments described herein.

Prodrug compounds of formula (I) are prepared via the route shown in Scheme 3.

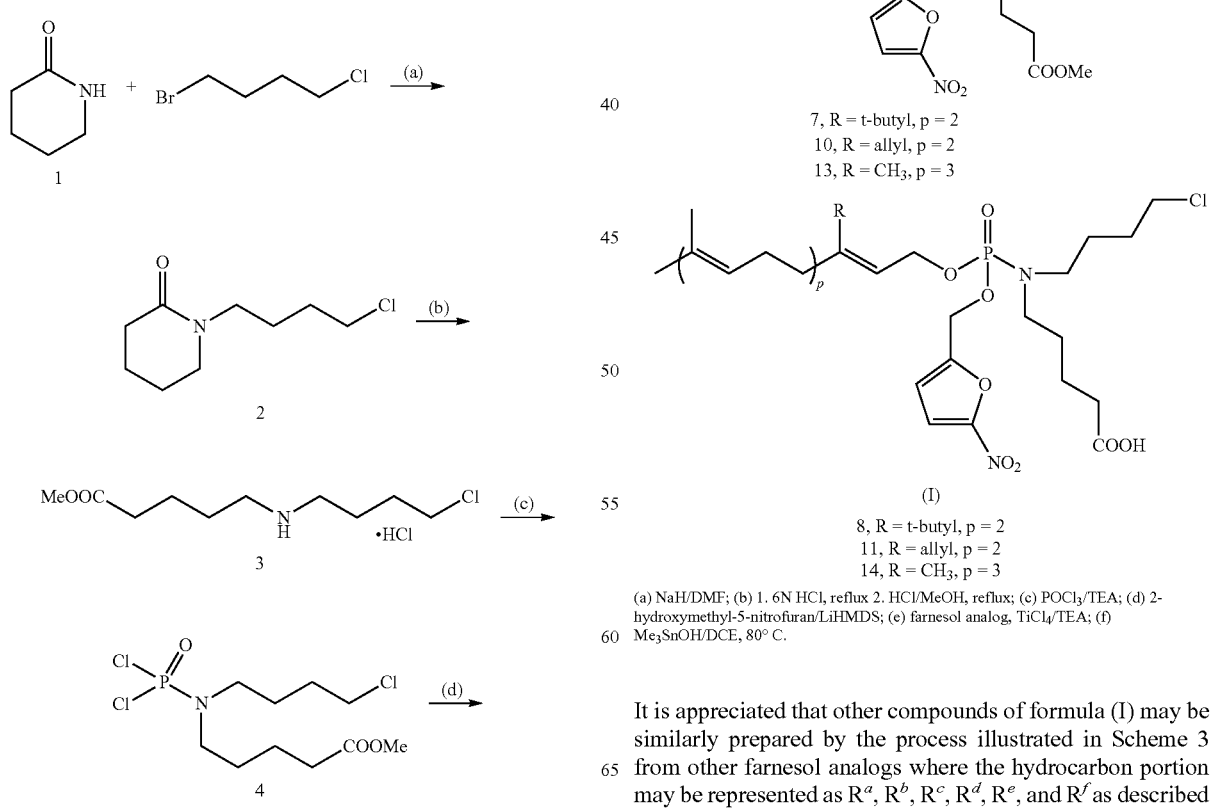

7, R = t-butyl, p = 2
10, R = allyl, p = 2
13, R = CH₃, p = 3

8, R = t-butyl, p = 2
11, R = allyl, p = 2
14, R = CH₃, p = 3

(a) NaH/DMF; (b) 1. 6N HCl, reflux 2. HCl/MeOH, reflux; (c) POCl₃/TEA; (d) 2-hydroxymethyl-5-nitrofuran/LiHMDS; (e) farnesol analog, TiCl₄/TEA; (f) Me₃SnOH/DCE, 80° C.

It is appreciated that other compounds of formula (I) may be similarly prepared by the process illustrated in Scheme 3 from other farnesol analogs where the hydrocarbon portion may be represented as $R^a$, $R^b$, $R^c$, $R^d$, $R^e$, and $R^f$ as described herein.

In another illustrative embodiment, prodrug compounds of formula (I) are prepared from a drug fragment described herein that includes a farnesol analog where the hydrocarbon portion is as set forth above for $R^a$ where $R^{11}$ is 3,3-dimethylallyl. This analog, compound C, is prepared according to the general synthesis shown in Scheme 4, and subsequently used to prepare compounds of formula (I) as described in Scheme 3.

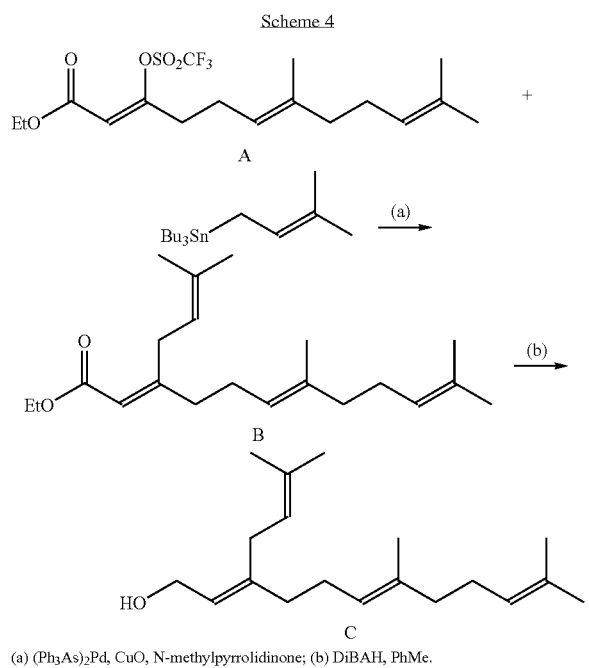

(a) (Ph$_3$As)$_2$Pd, CuO, N-methylpyrrolidinone; (b) DiBAH, PhMe.

It is appreciated that the above synthesis may be modified to allow the preparation of various analogs of the compound exemplified in Scheme 4, including, for example, other drug fragments described herein the hydrocarbon portion of which is as set forth above for $R^a$. For example, various alkyl and alkenyl tin reagents may be included in the synthesis of Scheme 4 to prepare the corresponding farnesol analogs.

In another illustrative embodiment, prodrug compounds of formula (I) are prepared from a drug fragment described herein that includes a farnesol analog where the hydrocarbon portion is as set forth above for $R^c$ where $R^{11}$ is methyl. This analog, compound F, is prepared according to the general synthesis shown in Scheme 5, and subsequently used to prepare compounds of formula (I) described in Scheme 3.

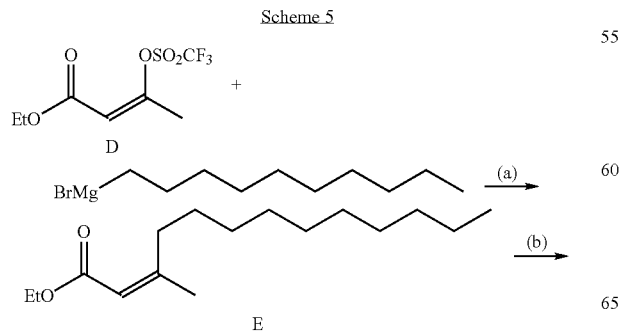

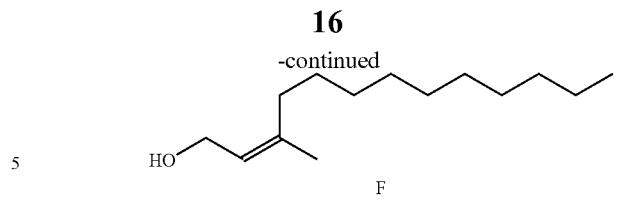

(a) CuCN, Et$_2$O; (b) DiBAH, PhMe.

It is appreciated that the above synthesis may be modified to allow the preparation of various analogs of the compound exemplified in Scheme 5, including, for example, other drug fragments described herein the hydrocarbon portion of which is as set forth above for $R^c$. For example, farnesol analogs with shorter or longer alkyl and alkenyl chains may be prepared by replacing the decyl-MgBr with other alkyl and alkenyl organometallic reagents.

In another illustrative embodiment, prodrug compounds of formula (I) are prepared from a drug fragment described herein that includes a farnesol analog where the hydrocarbon portion is as set forth above for $R^d$ where $R^{11}$ is 3,3-dimethylallyl and $R^{12}$ is para-biphenylethyl. This analog, compound J, is prepared according to the general synthesis shown in Scheme 6, and subsequently used to prepare compounds of formula (I) as described in Scheme 3.

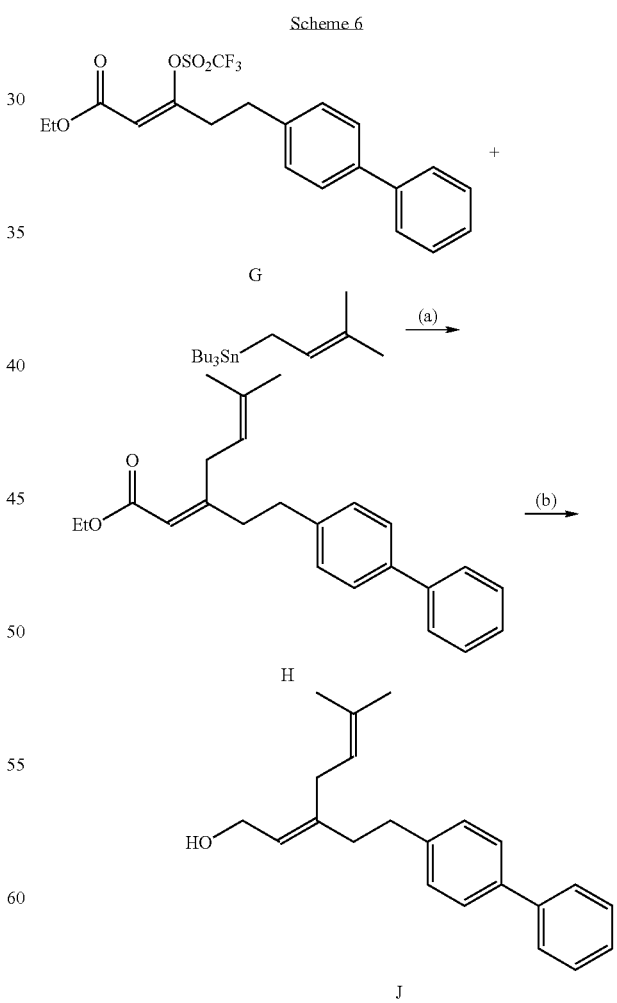

(a) (Ph$_3$As)$_2$Pd, CuO, N-methylpyrrolidinone; (b) DiBAH, PhMe.

It is appreciated that the above synthesis may be modified to allow the preparation of various analogs of the compound exemplified in Scheme 6, including, for example, other drug fragments described herein the hydrocarbon portion of which is as set forth above for $R^d$. For example, various alkyl and alkenyl tin reagents may be included in the synthesis of Scheme 6 to prepare the corresponding farnesol analogs.

In another illustrative embodiment, prodrug compounds of formula (I) are prepared from a drug fragment described herein includes a farnesol analog where the hydrocarbon portion is as set forth above for $R^e$ where $R^{11}$ is homoallyl and $R^{13}$ is methyl. This analog, compound L, is prepared according to the general synthesis shown in Scheme 7, and subsequently used to prepare compounds of formula (I) as described in Scheme 3.

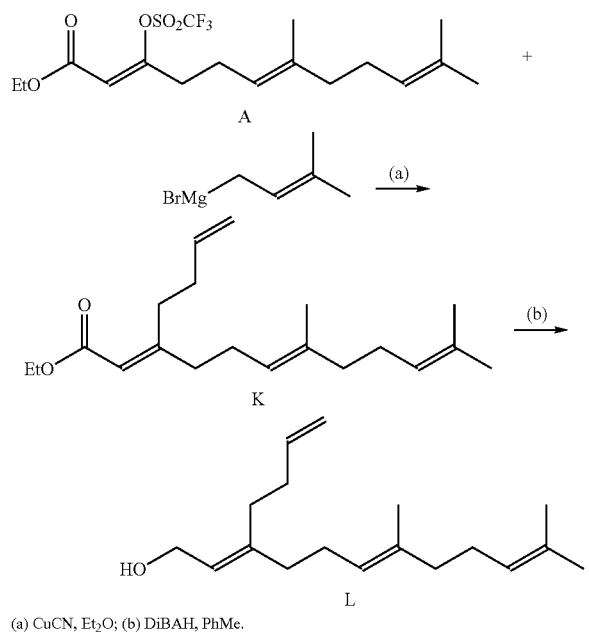

(a) CuCN, Et$_2$O; (b) DiBAH, PhMe.

It is appreciated that the above synthesis may be modified to allow the preparation of various analogs of the compound exemplified in Scheme 7, including, for example, other drug fragments described herein the hydrocarbon portion of which is as set forth above for $R^e$. For example, farnesol analogs with shorter or longer alkyl and alkenyl chains, for example compound CC, may be prepared by replacing the homoallyl-MgBr with other alkyl and alkenyl organometallic reagents.

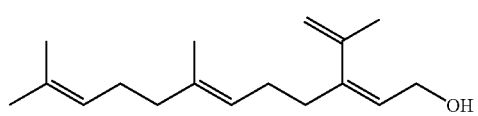

In another illustrative embodiment, prodrug compounds of formula (I) are prepared from a drug fragment described herein that includes a farnesol analog where the hydrocarbon portion is as set forth above for $R^e$ where $R^{11}$ is methyl, $R^{13}$ is 3,3-dimethylallyl, and p is 2. This analog, compound Q, is prepared according to the general synthesis shown in Scheme 8, and subsequently used to prepare compounds of formula (I) as described in Scheme 3.

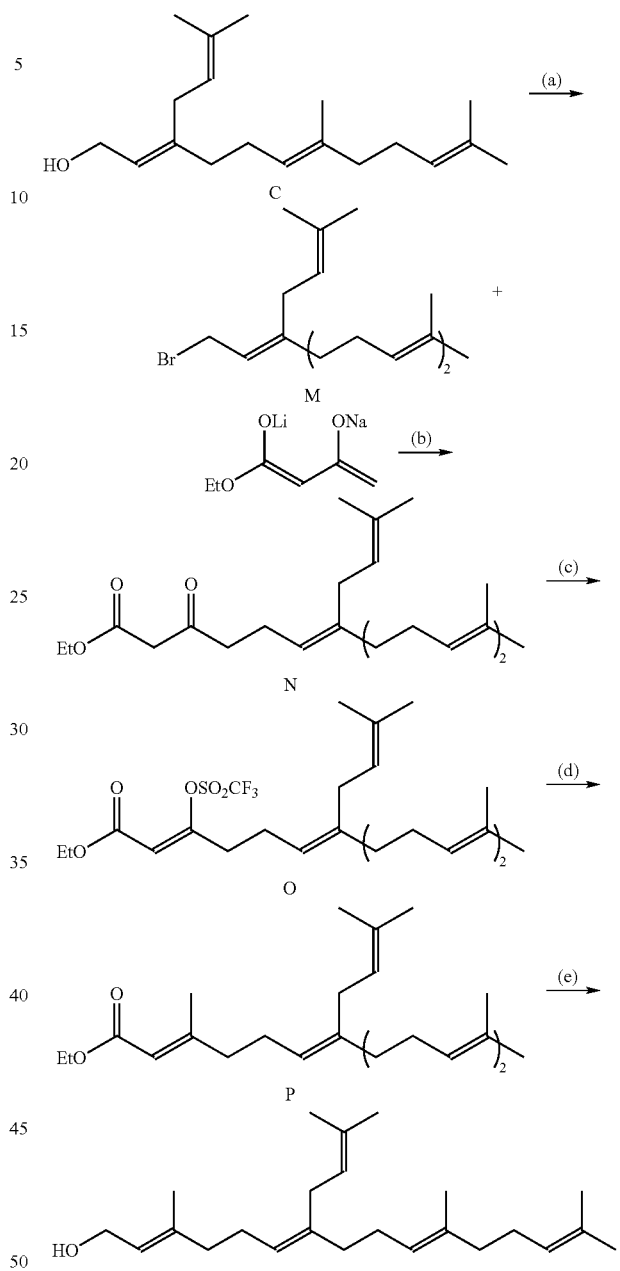

(a) CBr$_4$, Ph$_3$P, CH$_2$Cl$_2$; (b) THF, 0° C. to ambient; (c) 1. KHMDS, THF, 2. 6-chloropyridin-2-yl-N(SO$_2$CF$_3$)$_2$; (d) CH$_3$MgBr, CuCN, Et$_2$O; (e) DiBAH, PhMe.

It is appreciated that the above synthesis may be modified to allow the preparation of various analogs of the compound exemplified in Scheme 8, including, for example, other drug fragments described herein the hydrocarbon portion of which is as set forth above for $R^e$. For example, farnesol analogs with longer alkyl and alkenyl chains may be prepared by replacing the methyl-MgBr with other alkyl and alkenyl organometallic reagents.

In another illustrative embodiment, prodrug compounds of formula (I) are prepared from a drug fragment described herein that includes a farnesol analog where the hydrocarbon portion is as set forth above for $R^f$ where $R^{13}$ is methyl. This analog, compound T, is prepared according to the general synthesis shown in Scheme 9, and subsequently used to prepare compounds of formula (I) as described in Scheme 3.

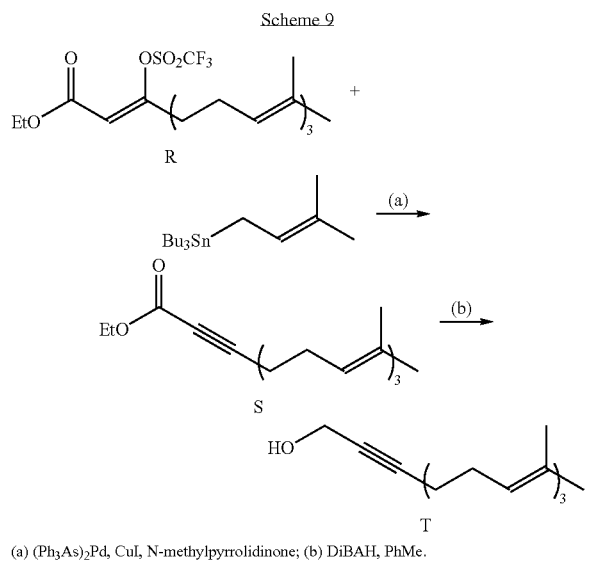

(a) (Ph₃As)₂Pd, CuI, N-methylpyrrolidinone; (b) DiBAH, PhMe.

It is appreciated that the above synthesis may be modified to allow the preparation of various analogs of the compound exemplified in Scheme 9, including, for example, other drug fragments described herein the hydrocarbon portion of which is as set forth above for $R^f$.

In another illustrative embodiment, prodrug compounds of formula (I) are prepared from a drug fragment described herein that includes a farnesol analog where the hydrocarbon portion is as set forth above for $R^e$ where $R^{11}$ is methyl, $R^{13}$ is 3,3-dimethylallyl, and p is 1. This analog, compound BB, is prepared according to the general synthesis shown in Scheme 10, and subsequently used to prepare compounds of formula (I) as described in Scheme 3.

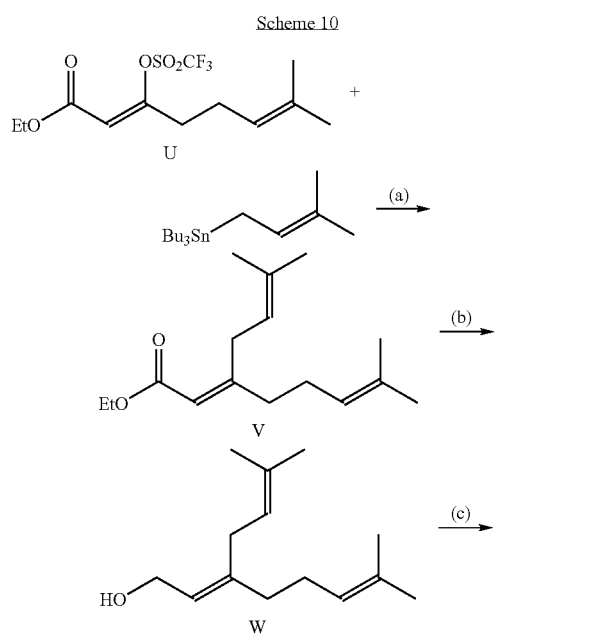

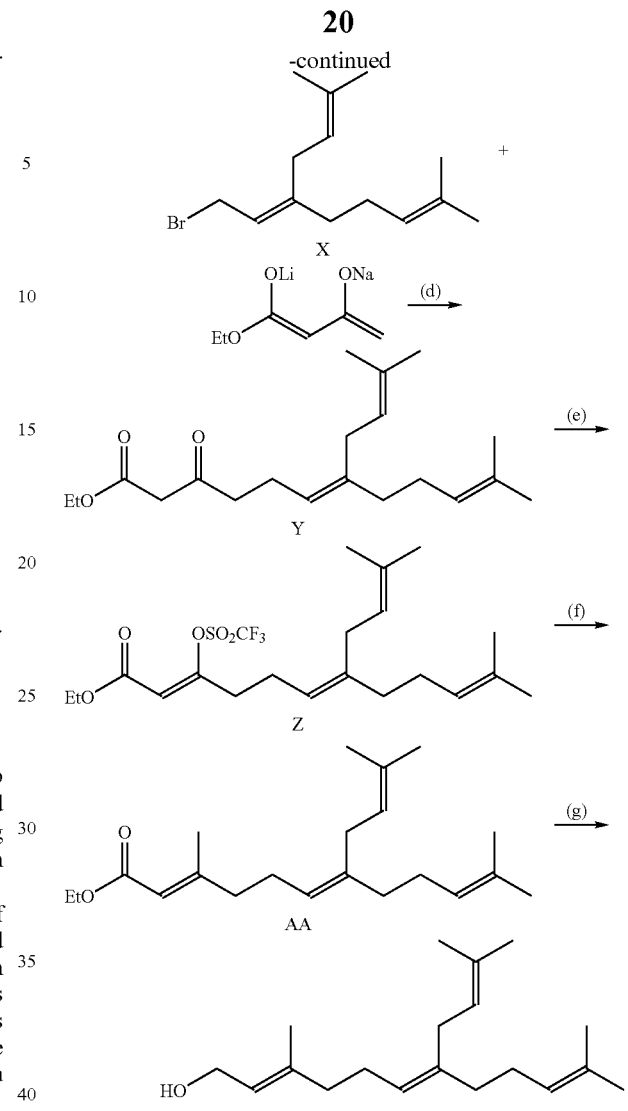

(a) (Ph₃As)₂Pd, CuO, N-methylpyrrolidinone; (b) DiBAH, PhMe; (c) CBr₄, Ph₃P, CH₂Cl₂; (d) THF, 0° C. to ambient; (e) 1. KHMDS, THF, 2. 6-chloropyridin-2-yl-N(SO₂CF₃)₂; (f) CH₃MgBr, CuCN, Et₂O; (g) DiBAH, PhMe.

It is appreciated that the above synthesis may be modified to allow the preparation of various analogs of the compound exemplified in Scheme 10, including, for example, other drug fragments described herein the hydrocarbon portion of which is as set forth above for $R^e$. For example, farnesol analogs with longer alkyl and alkenyl chains may be prepared by replacing the methyl-MgBr with other alkyl and alkenyl organometallic reagents.

In one illustrative embodiment a compound of formula II

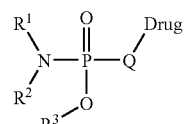

II or a pharmaceutically-acceptable salt thereof, is described wherein $R^1$ is —$(CR_2)_nY$; n is an integer from 2 to about 5; $R^2$ is —$(CR_2)_mX$; m is an integer from 2 to about 5; R is in each instance independently selected from the group consisting of hydrogen, alkyl, haloalkyl and fluoro; or any two R are taken together with the attached carbons to form a ring; X is a nucleophilically labile group; Y is a polar group; Q is selected from the group consisting of O, $NR^4$, $CR^9R^{10}$, $CF_2$, and a bond; wherein $R^4$ is hydrogen, alkyl, or acyl; $R^9$ and $R^{10}$ are independently selected from the group consisting of hydrogen, alkyl, haloalkyl, alkoxyl, and fluoro; or $R^9$ and $R^{10}$ along with the attached carbon form an optionally substituted ring; $R^3$ is a biologically labile ester forming group; and Drug is a prenyl group.

In another illustrative embodiment a compound of formula II, or a pharmaceutically-acceptable salt thereof, is described wherein Q is O. In another illustrative embodiment a compound of formula II, or a pharmaceutically-acceptable salt thereof, is described wherein Q is $NR^4$. In another illustrative embodiment, a compound of formula II, or a pharmaceutically-acceptable salt thereof, is described wherein Q is $CR^9R^{10}$ wherein $R^9$ and $R^{10}$ are independently selected from the group consisting of hydrogen, alkyl, haloalkyl, alkoxyl, and fluoro; or $R^9$ and $R^{10}$ along with the attached carbon form an optionally substituted ring. In another illustrative embodiment, a compound of formula II, or a pharmaceutically-acceptable salt thereof, is described wherein Q is $CF_2$. In another illustrative embodiment, a compound of formula II, or a pharmaceutically-acceptable salt thereof, is described wherein Q is a bond.

In another embodiment, any of the preceding compounds wherein Y is $CO_2H$ or a salt thereof is described.

In another embodiment, any of the preceding compounds wherein X is selected from the group consisting of halo, alkoxy, aryloxy, heteroaryloxy, acyloxy, arylsulfonyloxy, and alkylsulfonyloxy; each of which is optionally substituted is described.

In another embodiment, any of the preceding compounds wherein the integer n is 4 is described.

In another embodiment, any of the preceding compounds wherein the integer m is 4 or 5 is described.

In another embodiment, any of the preceding compounds wherein R is in each instance a hydrogen is described.

In another embodiment, any of the preceding compounds wherein X is chloro, bromo or iodo is described.

In another illustrative embodiment, a compound of formula II, or a pharmaceutically-acceptable salt thereof, is described wherein Q is $CR^9R^{10}$ and $R^9$ and $R^{10}$ are hydrogen.

In another illustrative embodiment, any of the preceding compounds wherein $R^3$ is heteroarylalkyl optionally substituted with an electron withdrawing group is described.

In another illustrative embodiment, any of the preceding compounds where Drug is represented by formula III

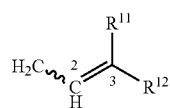

III wherein $R^{11}$ is alkyl, haloalkyl, alkenyl, haloalkenyl, alkynyl, aryl, heteroaryl, or arylalkyl; $R^{12}$ is alkyl, alkenyl, cycloalkyl, arylalkyl, arylalkenyl, heteroarylalkyl, heteroarylalkenyl, or $CH_2CH_2CH=CR^{13}(CH_2CH_2CH=C(CH_3))_p$, wherein p is 1, 2, or 3; and $R^{13}$ is alkyl, alkenyl, haloalkyl, haloalkenyl, or halide is described.

In another illustrative embodiment, any of the preceding compounds where Drug is represented by structure IV, and their pharmaceutically acceptable salts,

IV wherein $R^{12}$ is alkyl, alkenyl, cycloalkyl, arylalkyl, arylalkenyl, heteroarylalkyl, heteroarylalkenyl, or $CH_2CH_2CH=CR^{13}(CH_2CH_2CH=C(CH_3))_p$, wherein p is 1, 2, or 3; and $R^{13}$ is alkyl, alkenyl, haloalkyl, haloalkenyl, or halide are described.

In another illustrative example compounds and their pharmaceutically acceptable salts are described wherein Drug is represented by formula III where $R^{11}$ is alkyl, haloalkyl, alkenyl, haloalkenyl, or alkynyl; and $R^{12}$ is $CH_2CH_2CH=CR^{13}(CH_2CH_2CH=C(CH_3))_p$, where p is 1 or 2; and $R^{13}$ is methyl.

In another illustrative example compounds and their pharmaceutically acceptable salts are described wherein Drug is represented by formula III where $R^{11}$ is alkyl, haloalkyl, alkenyl, haloalkenyl, or alkynyl; and $R^{12}$ is $CH_2CH_2CH=CR^{13}(CH_2CH_2CH=C(CH_3))_p$, wherein p is 1 or 2, and $R^{13}$ is alkyl, haloalkyl, alkenyl, haloalkenyl, or alkynyl.

In another illustrative example compounds and their pharmaceutically acceptable salts are described wherein Drug is represented by formula III where $R^{11}$ is alkyl, haloalkyl, alkenyl, haloalkenyl, alkynyl, aryl, heteroaryl, or arylalkyl; and $R^{12}$ is $C_4$-$C_{15}$ alkyl.

In another illustrative example compounds and their pharmaceutically acceptable salts are described wherein Drug is represented by formula III where $R^{11}$ is alkyl, haloalkyl, alkenyl, haloalkenyl, or alkynyl; $R^{12}$ is $CH_2CH_2R^{14}$, where $R^{14}$ is selected from the group consisting of cyclohexyl, phenyl, aryl, heteroaryl, naphthyl, biphenyl, biaryl and bi-heteroaryl; each of which is optionally substituted.

In another illustrative example compounds and their pharmaceutically acceptable salts are described wherein Drug is represented by formula III where $R^{11}$ is alkyl, haloalkyl, alkenyl, haloalkenyl, or alkynyl; and $R^{12}$ is $CH_2CH_2CH=CR^{13}(CH_2CH_2CH=C(CH_3))_p$, wherein p is 1, 2 or 3; and $R^{13}$ is alkyl, haloalkyl, alkenyl, haloalkenyl, or alkynyl.

In another illustrative example compounds and their pharmaceutically acceptable salts are described wherein Drug is represented by formula III where $R^{11}$ is methyl; and $R^{12}$ is $CH_2CH_2CH=CR^{13}(CH_2CH_2CH=C(CH_3))_p$, wherein p is 1, 2 or 3; and $R^{13}$ is methyl.

In another illustrative example compounds and their pharmaceutically acceptable salts are described wherein Drug is represented by formula III where $R^{11}$ is allyl; and $R^{12}$ is $CH_2CH_2CH=CR^{13}(CH_2CH_2CH=C(CH_3))_p$, wherein p is 1, 2 or 3; and $R^{13}$ is methyl.

In another illustrative example compounds and their pharmaceutically acceptable salts are described wherein Drug is represented by formula III wherein $R^{11}$ is t-butyl; and $R^{12}$ is $CH_2CH_2CH=CR^{13}(CH_2CH_2CH=C(CH_3))_p$, wherein p is 1, 2 or 3; and $R^{13}$ is methyl.

In another illustrative example compounds and their pharmaceutically acceptable salts are described wherein Drug is represented by formula III wherein $R^{11}$ is 3,3-dimethylallyl; and $R^{12}$ is $CH_2CH_2CH=CR^{13}(CH_2CH_2CH=C(CH_3))_p$, wherein p is 1, 2 or 3; and $R^{13}$ is methyl.

In another illustrative example compounds and their pharmaceutically acceptable salts are described wherein Drug is represented by formula III wherein $R^{11}$ is alkyl, haloalkyl, alkenyl, haloalkenyl, alkynyl, aryl, heteroaryl, or arylalkyl; and $R^{12}$ is n-$C_{10}H_{23}$.

In another embodiment, a pharmaceutical composition comprising a therapeutically effective amount of any of the compounds or pharmaceutically acceptable salts thereof and an acceptable carrier, diluent, or excipient therefore is described.

In another embodiment, a method for treating a disease state arising from the dysfunction of an enzyme in a phosphate-dependent biological process in a mammal, said disease state being responsive to inhibition of the enzyme, the method comprising the step of administering to the mammal an amount of the compound of the above embodiments sufficient to generate an inhibitory concentration of an inhibitor of said enzyme is described. In another embodiment, the above method wherein the enzyme is a protein farnesyl transferase is described.

In another embodiment, any of the preceding compounds wherein m is 4, n is 4, R is in each instance hydrogen, X is chloro; and Y is $CH_2H$ or a salt thereof is described.

In one illustrative embodiment, pharmaceutical formulations comprising an effective amount of prodrug compounds for inhibition of FTase and concomitant treatment of cancers are described. As used herein, an effective amount of the prodrug compound with respect to the treatment of cancer refers to an amount of the compound capable of interfering with the spread of the cancer. For example, such interference may be manifested in slowing, stopping, or reversing the spread of the cancer; slowing, stopping, or reversing the growth or proliferation of cancer or malignant cells; or slowing, stopping, or reversing the growth of a solid tumor, and the like. In one aspect, effective amounts of compounds used in the methods described herein may be derived, or determined from data gathered by screening such compounds on the NCI panel of human tumor cell lines, the effective amount being related to that which inhibits growth and/or proliferation of tumor cells and/or kills malignant cells as a direct or indirect result of FTase inhibition.

The effective amount to be administered to a patient may be based on body surface area, patient weight, and/or patient condition. The interrelationship of dosages for animals and humans (based on milligrams per meter squared of body surface) is described by Freireich, E. J., et al., in *Cancer Chemother. Rep.* 1966, 50 (4): 219. Body surface area may be approximately determined from patient height and weight (see, for example, Scientific Tables, Geigy Pharmaceuticals, Ardley, New York, pages 537-538 (1970)). An effective amount of the prodrug compounds for use in treating cancer, can range from about 0.05 mg/kg to about 100 mg/kg, about 0.25 mg/kg to about 50 mg/kg, and illustratively about 0.1 to about 10 mg/kg per dose. Effective doses may also vary dependent on route of administration, excipient usage, and/or the possibility of co-usage with other therapeutic treatments, including other chemotherapeutic agents, and radiation therapy. However, it is to be understood that dosages may be ultimately determined by the treating physician.

Pharmaceutical formulations of the prodrugs described herein may be administered via any route, including a parenteral route, including subcutaneously, intraperitoneally, intramuscularly, and intravenously. Examples of parenteral dosage forms include aqueous solutions or suspensions of the active agent in isotonic saline, 5% glucose, or other pharmaceutically acceptable liquid carrier. In one aspect of the pharmaceutical compositions described herein, the compound is dissolved in a saline solution containing 5% of dimethyl sulfoxide and about 10% Cremophor™ EL (Sigma Chemical Company). Additional solubilizing agents such as cyclodextrins, which can form more soluble complexes with the present compounds, or other solubilizing agents can be utilized as pharmaceutical excipients for delivery of the present compounds for cancer therapy.

Alternatively, the present compounds can be formulated into dosage forms for other routes of administration utilizing conventional methods. The pharmaceutical compositions can be formulated, for example, in dosage forms for oral administration in a capsule, a gel seal, or a tablet. Capsules may comprise any pharmaceutically acceptable material such as gelatin or cellulose derivatives. Tablets may be formulated in accordance with conventional procedure by compressing mixtures of the active prodrugs and solid carriers and lubricants. Examples of solid carriers include starch, sugar, and bentonite. The compounds described herein can also be administered in a form of a hard shell tablet or capsule containing, for example, lactose or mannitol as a binder and conventional fillers and tableting agents.

In another illustrative embodiment, the prodrugs described herein may be used in methods for treating various cancers. Evaluation of the prodrugs described herein useful for treating cancer may involve in vitro studies that measure cytotoxicity of the prodrugs against various cancer cell lines. In one illustrative aspect, the cancer cell is an STS-26T human neurofibrosarcoma cell.

EXAMPLES

The following examples are intended to further illustrate the compounds described herein as prodrugs, and the synthesis and biological activity thereof, and should not be interpreted, considered, or understood to limit the invention in any way. Illustratively, modifications of the following examples are contemplated, including modifications of the drug or drug analog, or fragment of a drug-phosphate conjugate or analog thereof. Such other drugs may be prepared as pro-drugs based on the examples described herein. Examples of chemical transformations that may be used in the synthesis of additional illustrative prodrugs of the invention are also described. When included in the following examples, the disclosures of the citations are incorporated herein by reference for all they describe regarding the chemical transformation that is the subject of the example. Other farnesol analogs described herein may be synthesized by conventional methods. Farnesol analogs which contain aryl, including naphthyl, or biphenyl groups as depicted above were synthesized as described herein following the method described by Zhou, et al., in Bioorg. Med. Chem. Lett. 2002, 12, 1417-1420, the disclosure of which is incorporated herein by reference. The allyl- and homoallyl-containing farnesol analogs and related compounds were synthesized as described herein following the method described by Gibbs, et al., in *J. Med. Chem.* 1999, 42, 3800-3808, the disclosure of which is incorporated herein by reference. The synthesis of many of the other compounds described herein occurred with only minor modification of the synthesis described by Xie, et al., in *J. Org. Chem.* 2000, 65, 8552-8563, the disclosure of which is incorporated herein by reference.

Example 1

Methyl 5-(4-chlorobutyl)aminopentanoate hydrochloride (3)

1-(4-Chlorobutyl)-2-piperidinone 2 (1.9 g, 10 mmol) was dissolved in 6 N HCl (60 mL) and refluxed for 24 h. It was cooled to room temperature, diluted with MeOH (50 mL) and evaporated at reduced pressure. The methanol dilution and evaporation was repeated. The resultant oily material was azeotroped with toluene 3×50 mL and then dissolved in saturated HO/MeOH (20 mL) and refluxed for 3 h. The solution was evaporated at reduced pressure, and the residue was twice dissolved in MeOH (20 mL) and evaporated to dryness. The crude product 3 was carried on to the next step without purification. Yield: 2.44 g, 95%; $^1$H NMR (CD$_3$OD, 300 MHz): δ 3.6 (s, 3H, Me), 3.5 (m, 2H, CH$_2$—Cl), 2.9 (m, 4H, —CH$_2$—N—CH$_2$), 2.4 (t, 2H, —CH$_2$—CO), 1.9-1.5 (m, 8H); MS, (EI): 221/223; HRMS: calculated for C$_{10}$H$_{20}$Cl NO$_2$ 221.1183, found 221.1184.

Example 2

Phosphoramidic Dichloride (4)

A solution of 3 (1.7 g, 6.59 mmol) in DCM (13 mL) was cooled to 0° C. POCl$_3$ (0.9 mL, 9.89 mmol) was added followed by a solution of TEA (2.6 mL, 19.77 mmol) in DCM (5 mL). The solution was allowed to warm gradually to room temperature and stirred for 3 h. Saturated ammonium chloride (25 mL) and DCM (50 mL) were added. The layers were separated, the aqueous layer was extracted with DCM (2×50 mL), and the collected organic layers were dried over MgSO$_4$. Removal of the solvent gave an oil which was purified by silica gel chromatography (1:4 ethyl acetate:hexanes) to give 4 (1.08 g, 48%). $^1$H NMR (CDCl$_3$, 300 MHz) δ 3.7 (s, 3H, Me), 3.6 (m, J=2.1 Hz, 2H, CH$_2$—Cl), 3.2 (m, 4H, —CH$_2$—N—CH$_2$), 2.4 (m, 2H, —CH$_2$—CO), 1.7 (m, 4H), 1.6 (m, 4H); $^{31}$P NMR (CDCl$_3$, 121 MHz): −7.6 ppm.

Example 3

Phosphoramidic Chloride (5)

LiHMDS (2.29 mL, 1 M solution in THF, 2.29 mmol) was added dropwise to a solution of 2-hydroxymethyl-5-nitrofuran (0.333 g, 2.29 mmol) in THF at −78° C. After 10 min at −78° C., a solution of 4 (0.771 g, 2.29 mmol) in THF was added. The reaction mixture was warmed to −65° C. and stirred for 1 h, then quenched by the addition of 20 mL saturated ammonium chloride. The solution was extracted with DCM (2×20 mL) and dried over Na$_2$SO$_4$. Purification by silica gel chromatography (1:9 ethyl acetate:hexanes) afforded 5 (0.51 g, 50%). The structure of 5 was verified by $^1$H NMR, and the product was then taken directly to the next step. $^1$H NMR (CDCl$_3$, 300 MHz): δ 7.3 (d, J=3.6 Hz, 1H, Ar—H), 6.7 (d, J=3.6 Hz, 1H, Ar—H), 5.1 (m, 2H, O—CH$_2$—), 3.6 (s, 3H, Me), 3.5 (t, J=6.3 Hz, 2H, CH$_2$—Cl), 3.2 (m, 4H, —CH$_2$—N—CH$_2$), 2.3 (t, J=6.9 Hz, 2H, —CH$_2$—CO), 1.7-1.6 (m, 8H); $^{31}$P NMR (CDCl$_3$, 121 MHz): —8.4 ppm.

Example 4

Phosphoramidate Ester (7)

To a solution of 5 (0.36 g, 0.81 mmol), 3-tert-butyl-3-desmethylfarnesol 6 (0.242 g, 0.916 mmol) and TEA (145 µl, 1.03 mmol) in THF (2 mL) was added TiCl$_4$(1M in THF, 80 µl, 0.08 mmol) at room temperature. The reaction mixture was stirred for 1 h and then was filtered, concentrated, and purified by silica gel chromatography (1:1 ethyl acetate:hexanes) to give 7 (294 mg, 58%) as an oil. $^1$H NMR (CDCl$_3$, 300 MHz): δ 7.3 (d, J=2.7 Hz, 1H, Ar—H), 6.7 (d, J=2.7 Hz, 1H, Ar—H), 5.2 (t, J=6 Hz, 1H), 5.1 (m, 2H), 5.0 (d, J=8.7 Hz, 2H, allylic O—CH$_2$), 4.7 (m, 2H, O—CH$_2$—Ar), 3.6 (s, 3H, COOMe), 3.5 (t, J=6.3 Hz, 2H, CH$_2$—Cl), 3.0 (m, 4H, —CH$_2$—N—CH$_2$), 2.3 (t, J=6.9 Hz, 2H, —CH$_2$—CO), 2.1-1.9 (m, 8H), 1.8-1.5 (m, 17H); 1.1 (s, 9H); $^{31}$P NMR (CDCl$_3$, 121 MHz): −14.5 ppm; $^{13}$C NMR (CDCl$_3$, 75 MHz): δ169.4, 148.9, 148.8, 146.4, 130.9, 127.0, 119.9, 119.4, 116.1, 108.3, 107.6, 60.0, 54.8, 47.1, 40.9, 40.5, 40.2, 35.3, 31.6, 31.3, 29.2, 26.1, 25.3, 24.6, 23.5, 22.3, 21.3, 17.7, 13.3, 11.7; MS (ESI): 695/697 (M+Na)$^+$; HRMS: calculated for C$_{33}$H$_{54}$Cl N$_2$O$_8$P 695.3204, found 695.3207.

Example 5 t-butylfarnesyl Prodrug (8)

A solution of 7 (0.348 g, 0.518 mmol) in 1,2-dichloroethane (5 mL) was treated with trimethyltin hydroxide (0.372 g, 2.067 mmol) and heated at 80° C. for 20 h. The solution was evaporated to dryness at reduced pressure, and the residue was dissolved in ethyl acetate (100 mL) and washed with 5% HCl (4×50 mL) and with brine (1×75 mL) and dried over Na$_2$SO$_4$. The product was purified by silica gel chromatography (0.1% AcOH/ethyl acetate) to give 8 (107 mg, 32%). $^1$H NMR (CDCl$_3$, 300 MHz): δ 7.3 (d, J=3.3 Hz, 1H, Ar—H), 6.6 (d, J=3.3 Hz, 1H, Ar—H), 5.2 (t, J=6.3 Hz, 1H), 5.1 (m, 2H), 5.0 (d, J=8.4 Hz, 2H, allylic O—CH$_2$), 4.7 (m, 2H, O—CH$_2$—Ar), 3.5 (t, J=6.3 Hz, 2H, CH$_2$—Cl), 3.1 (m, 4H, —CH$_2$—N—CH$_2$), 2.3 (t, J=6.9 Hz, 2H, —CH$_2$—CO), 2.1-1.9 (m, 8H), 1.8-1.6 (m, 17H); 1.1 (s, 9H); $^{31}$P NMR (CDCl$_3$, 121 MHz): −14.8 ppm; $^{13}$C NMR (CDCl$_3$, 75 MHz): δ173.2, 148.8, 148.7, 146.6, 130.9, 126.9, 119.9, 119.4, 115.6, 108.5, 107.6, 60.2, 55, 40.9, 40.6, 40.2, 34.8, 31.6, 31.3, 29.1, 26.1, 25.3, 24.5, 23.5, 22.3, 21.3, 17.5, 13.3, 11.7.

Example 6

Phosphoramidate Ester (10)

To a solution of 5 (0.20 g, 0.45 mmol), 3-allyl-3-desmethyl farnesol 9 (0.124, 0.5 mmol) and TEA (80 µl, 0.585 mmol) in THF (1.1 mL) was added TiCl$_4$ (1M in THF, 45 µl, 0.45 mmol) at room temperature. After 1 h, the solution was filtered, concentrated, and purified by silica gel chromatography (1:1 ethyl acetate:hexanes) to give 10 (119 mg, 40%) as an oil. $^1$H NMR (CDCl$_3$, 300 MHz): δ 7.3 (d, J=3.6 Hz, 1H, Ar—H), 6.6 (d, J=3.6 Hz, 1H, Ar—H), 5.7 (m, 1H), 5.4 (t, J=6.8 Hz, 1H), 5.1-5.0 (m, 4H), 4.9 (d, J=8.4 Hz, 2H), 4.5 (m, 2H), 3.7 (s, 3H, COOMe), 3.5 (t, J=7.5 Hz, 2H, CH$_2$—Cl), 3.0 (m, 4H, —CH$_2$—N—CH$_2$), 2.8 (d, J=6 Hz, 2H, allylic CH$_2$), 2.3 (t, J=7.2 Hz, 2H, —CH$_2$—CO), 2.1-1.9 (m, 8H), 1.7-1.5 (m, 17H); $^{31}$P NMR (CDCl$_3$, 121 MHz): −14.0 ppm; $^{13}$C NMR (CDCl$_3$, 75 MHz): δ169.3, 148.9, 148.8, 139.3, 131.2, 130.9, 127.0, 119.9, 119.1, 115.8, 115.7, 111.6, 108.3, 107.6, 58.7, 54.9, 47.2, 40.9, 40.5, 40.2, 35.3, 32.6, 30.8, 29.2, 23.5, 23.3, 22.3, 21.9, 21.3, 17.7, 13.3, 11.7.

Example 7

Allylfarnesyl Prodrug (11)

A solution of 10 (0.114 g, 0.174 mmol) in 1,2-dichloroethane (1.4 mL) was treated with trimethyltin hydroxide (0.157 g, 0.869 mmol) and heated at 80° C. for 20 h. The solvent was removed at reduced pressure, and the residue was dissolved in ethyl acetate (20 mL) and washed with 5% HCl (4×10 mL) and with brine (1×20 mL) and dried over Na$_2$SO$_4$. The product was purified by silica gel chromatography (0.1% AcOH/ethyl acetate) to give 11 (28 mg, 28%). $^1$H NMR (CDCl$_3$, 300 MHz): δ 7.26 (m, Ar—H+ CDCl$_3$), 6.7 (d, J=4.2 Hz, 1H, Ar—H), 5.7 (m, 1H), 5.5 (t, J=3.6 Hz, 1H), 5.1-4.9 (m, 6H), 4.6 (m, 2H), 3.5 (t, J=6.3 Hz, 2H, CH$_2$—Cl), 3.1 (m, 4H, —CH$_2$—N—CH$_2$), 2.8 (d, J=5.4 Hz, 2H, allylic CH$_2$), 2.3 (t, J=6 Hz, 2H, —CH$_2$—CO), 2.0-1.9 (m, 8H), 1.7-1.6 (m, 17H); $^{31}$P NMR (CDCl$_3$, 121 MHz): —14.1 ppm; $^{13}$C NMR (CDCl$_3$, 75 MHz): δ 171.6, 148.7, 148.6, 139.5, 131.3, 130.9, 127.0, 119.9, 119.1, 115.6, 111.6, 108.4, 107.6, 58.8, 54.9, 40.7, 40.2, 35.3, 32.6, 30.8, 28.7, 25.2, 23.4, 22.3, 21.9, 21.3, 17.4, 13.3, 11.7.

Example 8

Phosphoramidate Ester (13)

To a solution of 5 (0.136 g, 0.0307 mmol), Z,E,E-geranylgeraniol 12 (0.093 g, 0.338 mmol) and TEA (56 µl, 0.4 mmol) in THF (1 mL) was added TiCl$_4$ (1M in THF, 30 µl, 0.03 mmol) at room temperature. After 1 h, the solution was filtered, concentrated, and purified by silica gel chromatography (1:1 ethyl acetate:hexanes) to give 13 (93 mg, 43%) as an oil. $^1$H NMR (CDCl$_3$, 300 MHz): δ 7.3 (d, J=3.6 Hz, 1H, Ar—H), 6.6 (d, J=3.6 Hz, 1H, Ar—H), 5.4 (t, J=6.9 Hz, 1H), 5.1 (m, 3H), 5.0 (d, J=8.4 Hz, 2H, allylic O—CH$_2$), 4.8 (m, 2H, O—CH$_2$—Ar), 3.7 (s, 3H, COOMe), 3.5 (t, J=6.3 Hz, 2H, CH$_2$—Cl), 3.0 (m, 4H, —CH$_2$—N—CH$_2$), 2.3 (t, J=6.9 Hz, 2H, —CH$_2$—CO), 2.1-1.5 (m, 35H); $^{31}$P NMR (CDCl$_3$, 121 MHz): −14.0 ppm; $^{13}$C NMR (CDCl$_3$, 75 MHz): δ169.3, 149.0, 148.9, 138.2, 131.6, 130.7, 126.9, 119.9, 119.7, 118.8, 115.5, 108.2, 107.6, 58.6, 54.8, 47.1, 40.9, 40.5, 40.2, 35.3, 29.1, 27.8, 25.2, 23.5, 22.4, 22.3, 21.3, 19.2, 17.7, 13.3, 11.6.

Example 9

Z, E, E Geranylgeranyl Prodrug (14)

A solution of 13 (0.091 g, 0.125 mmol) in 1,2-dichloroethane (1.3 mL) was treated with trimethyltin hydroxide (0.113 g, 0.626 mmol) and heated at 80° C. for 20 h. The solvent was removed at reduced pressure, and the residue was dissolved in ethyl acetate (100 mL) and washed with 5% HCl (4×25 mL) and with brine (1×50 mL) and dried over Na$_2$SO$_4$. The product was purified by silica gel chromatography (0.1% AcOH/ethyl acetate) to give 14 (10 mg, 11%).

Example 10

Biological Activity of Farnesylated Monophosphates

In order to demonstrate proof of principle that farnesylated monophosphates can serve as potent inhibitors of FTase, 3-allylfarnesyl monophosphate, 3-(3,3-dimethylallyl)farnesyl monophosphate, and 3-t-butylfarnesyl monophosphate were evaluated in vitro for the ability to inhibit FTase. 3-Allylfarnesyl monophosphate and 3-t-butylfarnesyl monophosphate displayed potent, low nanomolar inhibition of FTase, exhibiting IC$_{50}$ values of ~11 nM and ~16 nM, respectively. However, 3-(3,3-dimethylallyl)farnesyl monophosphate was less potent, not showing 50% inhibition at the highest dose tested (10 uM), which is consistent with 3-(3,3-dimethylallyl)farnesyl pyrophosphate being a protein-selective inhibitor of FTase.

Example 11

Ethyl 3-(3-methyl-1-but-2-enyl)-7,11-dimethyldodeca-2Z,6E,10-trienoate (Compound B): Ph$_3$As (18.5 mg, 0.06 mmol), Pd(II) (12.8 mg, 0.033 mmol), and CuO (5.28 mg, 0.06 mmol) were charged in a round bottom flask. To this dry mixture was added 1.0 mL of NMP, and the resulting suspension was stirred at room temperature for 5 min under argon atmosphere. Then a solution of triflate A (200 mg, 0.604 mmol) in 0.5 mL NMP was added dropwise. After 5 min at rt, tributyl(3-methyl-2-butenyl)tin (282 mg, 0.79 mmol) was added, the reaction mixture was heated to 110° C. and stirred at that temperature for 12 hr. It was then cooled, taken up in ethyl acetate (25 mL), and washed with aqueous KF (2×20 mL) and H$_2$0 (2×20 mL). The aqueous layers were back extracted with ethyl acetate (30 mL), and the combined organic layers were dried (MgSO$_4$), filtered, and concentrated. Purification by flash chromatography (hexane/ethyl acetate 98:2) gave B, in a 78% yield. $^1$H NMR (CDCl$_3$): δ1.19 (t, J=14.1 Hz, 3H, CH$_2$CH$_3$), 1.51 (s, 6H, 2CH$_3$), 1.56-1.62 (s, 9H, 3CH$_3$), 1.89-2.06 (m, 8H, 3CH$_2$), 3.29 (d, J=7.5 Hz, 2H, CH$_2$), 4.07 (q, J=21.3 Hz, 2H, OCH$_2$), 5.03 (m, 3H, 3CH), 5.56 (s, 1H, CH). $^{13}$C NMR (CDCl$_3$): δ14.27, 15.95, 17.62, 17.95, 25.62, 25.71, 26.09, 26.6, 30.92, 37.84, 39.62, 59.45, 115.18, 120.98, 123.05, 124.19, 128.59, 133.66, 135.93, 162.59, 166.56. GC-MS (Ret. Time: 8.884 min) CI (m/z): 319 (M$^+$+H). Anal. Calcd. for C$_{21}$H$_{34}$O$_2$: C 79.20, H 10.77; found: C 79.59, H 10.93.

Example 12

3-(3-methyl-1-but-2-enyl)-7,11-dimethyldodeca-2Z,6E,10-trien-1-ol (Compound C): A solution of the ester B (1 equivalent) in toluene (6 mL/mmol; HPLC grade dried over 4 Å sieves) was treated at −78° C. under argon with diisobutylaluminum hydride (3 equivalents; 1.0 M in toluene). After the addition, the mixture was stirred for 1 h at −78° C. The reaction was quenched by adding the solution to saturated aqueous potassium sodium tartrate (40 mL), the organic phase was separated, and the aqueous phase was extracted with ethyl acetate (3×30 mL). The combined organic layers were washed with water (20 mL) and brine (20 mL) and dried by MgSO$_4$. Filtration and concentration followed by flash chromatography (hexane/ethyl acetate 9:1) gave C, in yields of 75-90%. This compound was characterized by $^1$H (proton) and $^{13}$C (carbon-13) NMR, and by MS.

Example 13 cis, trans-Farnesol was synthesized following the method described be Xie et al. in *J. Org. Chem.* 2000, 65, 8552-8563, the disclosure of which is hereby incorporated by reference.

Example 14 trans, cis-Farnesol was synthesized following the method described by Xie et al. in *J. Org. Chem.* 2000, 65, 8552-8563.

Example 15

(2Z,6E,10)-3-allyl-7,11-dimethyldodeca-2,6,10-trien-1-ol was synthesized following the method described by Gibbs et al. in *J. Med. Chem.* 1999, 42, 3800-3808, the disclosure of which is hereby incorporated by reference.

Example 16

(2Z,6E,10)-3-t-butyl-7,11-dimethyldodeca-2,6,10-trien-1-ol was synthesized following the method described by Mu et al. in *J. Org. Chem.* 1996, 61, 8010-8015, the disclosure of which is hereby incorporated by reference.

Example 17

3-Methyl-5-(4-phenyl)phenylpent-2-en-1-ol was synthesized following the method described by Zhou et al. in *Bioorg. Med. Chem. Lett.* 2002, 12, 1417-1420, the disclosure of which is hereby incorporated by reference.

Example 18

3-(3-Methyl-1-but-2-enyl)-7,11,15-trimethylhexadeca-2Z,6E,10E,14-tetraen-1-ol was synthesized from known ethyl 3-(trifluoromethylsulfonyl)-7,11,15-trimethylhexadeca-2Z,6E,10E,14-tetraenoate (see, Mu et al. in *Bioorg.*

*Med. Chem.* 2002, 10, 1207-1219, the disclosure of which is hereby incorporated by reference) using exactly the same procedures described above for the synthesis of compound C.

Example 19

Ethyl 3-(trifluoromethylsulfonyl)-but-2E-enoate (Triflate D): Dissolve sodium ethyl acetoacetate (1.0 mmol) in DMF and cool to 0° C. Once cool, add potassium bis(trimethylsilyl) amide (KHMDS, 1.1 mmol) dropwise. After five minutes has elapsed, the 2-[N,N-bis(trifluoromethylsulfonyl)amino]-5-chloropyridine (1.2 mmol) was added. The reaction was warmed to room temperature over 12 hours. The solution is diluted with ether and the reaction was quenched with 10% aqueous citric acid solution. The aqueous layer was extracted with ether (3×15 mL). The organic layers were combined, washed with brine (30 mL), dried with $MgSO_4$, filtered and concentrated. The crude mixture was purified by flash chromatography (hexanes/ethyl acetate 99:1) to give triflate D in a 61% yield (161 mg). $^1H$ NMR (300 MHz, $CDCl_3$): δ 0.8 (t, 3H), 1.3 (s, 3H), 4.2 (q, 2H) and 5.9 (s, 1H).

Example 20

Ethyl 3-methyltridec-2E-enoate (Compound E): Decyl magnesium bromide (2.4 mL of a 2.0 M soln in ether, 4.8 mmol) CuCN (221 mg, 2.49 mmol) were suspended in anhydrous ether and cooled to −78° C. The mixture was warmed to 0° C. for 5 minutes and cooled to −78° C. The triflate D (220 mg, 0.83 mmol) was dissolved in anhydrous ether and added to the decyl magnesium and CuCN solution dropwise. The mixture was stirred vigorously for 2.5 hours. The solution was then warmed to 0° C. and quenched with a 10% aqueous ammonium chloride solution. The layers were separated, and the aqueous layer was extracted with ethyl acetate (3×10 mL). The organic layers were combined, dried ($MgSO_4$), filtered and concentrated. Purification by flash chromatography (19:1 hexane/ethyl acetate) gave E in a yield of 75% (150 mg). $^1H$ NMR (300 MHz, $CDCl_3$): δ 0.8 (t, 3H), 1.25 (narrow m, 20H), 1.4 (s, 3H), 1.6 (2H), 3.6 (t, 3H), 4.2 (q, 2H) and 5.9 (s, 1H).

Example 21

3-Methyl-tridec-2E-en-1-ol (Compound F): Compound E (0.19 mmol) was dissolved in anhydrous toluene (3 mL) and chilled to −78° C. DIBAL-H (0.585 mmol, 2.0 M in toluene) was added dropwise. The solution reacted for 45 minutes and was warmed slightly. The reaction was quenched with 10% aqueous sodium potassium tartarate. The layers were separated and the aqueous layer was extracted (3×20 mL) with ethyl acetate. The organic layers were combined, washed with brine (10 mL), dried, filtered and concentrated. Purification by flash chromatography (9:1 hexane/ethyl acetate) gave F in yields of 85-90%. $^1H$ NMR (300 MHz, $CDCl_3$): δ 0.8 (t, 3H), 1.25 (narrow m, 20H), 1.5 (s, 3H), 1.8 (narrow m, 2H), 4.0 (d, 2H), and 5.4 (t, 1H).

Example 22

Ethyl 3-(But-3-methyl-2-en-1-yl)-5-(4-phenyl)phenyl-pent-2E-enoate (Compound H): Triflate G (350 mg, 0.78 mmol), CuO (620 mg, 7.8 mmol), $Ph_3$-As (23 mg, 0.078 mmol), and bis(benzonitrile)-palladium (II) chloride (16.5 mg, 0.0429 mmol) were placed in an argon-flushed flask and dissolved in NMP (6 mL). The mixture was immersed in an oil bath maintained at a temperature of 100-104° C., (3-methylbut-2-enyl)tributyltin (0.393 mL, 1.17 mmol) was added, and the reaction mixture was stirred for 12 h. It was then cooled, taken up in ethyl acetate (25 mL), and washed with aqueous KF (2.20 mL) and $H_2O$ (2×20 mL). The aqueous layers were back extracted with ethyl acetate (30 mL), and the combined organic layers were dried ($MgSO_4$), filtered and concentrated. Purification by flash chromatography (hexane/ethyl acetate 98:2) gave H in an 83% yield (230 mg). $^1H$ NMR (300 MHz, $CDCl_3$): δ 1.3 (t, 3H), 1.8 (t, 6H), 2.5 (t, 2H), 2.9 (t, 2H), 3.6 (d, 2H), 4.3 (q, 2H), 5.3 (t, 1H), 5.8 (t, 1H), 7.2 (t, 2H), 7.3 (t, 1H), 7.35 (d, 2H), 7.45 (d, 2H), and 7.5 (d, 2H).

Example 23

3-(But-3-methyl-2-en-1-yl)-5-(4-phenyl)phenylpent-2-en-1-ol (Compound J): Compound H (230 mg, 0.65 mmol) was dissolved in anhydrous toluene (3 mL) and chilled to −78° C. A lM solution of DIBAL-H (1.83 mL, 1.83 mmol) was added dropwise. The solution reacted for 1 hour and was warmed slightly. The reaction was quenched with 10% aqueous sodium potassium tartarate. The layers were separated and the aqueous layer was extracted (3×20 ml) with ethyl acetate. The organic layers were combined, washed with brine (10 mL), dried, filtered and concentrated. Purification by flash chromatography (hexane/ethyl acetate 90:10) gave alcohol J, in a 76% yield (150 mg). $^1H$ NMR (300 MHz, $CDCl_3$): δ 1.8 (t, 6H), 2.5 (t, 2H), 2.9 (t, 2H), 3.6 (d, 2H), 4.1 (d, 2H), 5.3 (t, 1H), 5.8 (t, 1H), 7.2 (t, 2H), 7.3 (t, 1H), 7.35 (d, 2H), 7.45 (d, 2H) and 7.5 (d, 2H).

Example 24

3-(But-3-en-1-yl)-7,11-dimethyldodeca-2E,6E,10-trienoate ethyl ester (Compound K): Copper cyanide (325 mg, 3.66 mmol) was suspended in ether and chilled to −78° C. The homoallyl magnesium bromide reagent (4.88 mL of a 0.5 M solution, 2.44 mmol) was added and the mixture was warmed to 0° C. for five minutes. The mixture was again chilled to −78° C. and triflate A (500 mg, 1.22 mmol) was added to the reaction slowly. After 90 minutes the reaction was warmed to 0° C. and quenched with 10% aq. ammonium chloride. The organic layer and the aqueous layers were separated and the aqueous layer was extracted three times with ether. The organic layers were combined, dried with magnesium sulfate, filtered and concentrated under reduced pressure. The product was purified using flash chromatography with 1% ethyl acetate in hexanes to produce the ester K in an 84% yield (313 mg). $^1H$ NMR (300 MHz, $CDCl_3$): δ 1.1 (t, 3H), 1.45 (s, 3H), 1.55 (s, 3H), 1.9 (m, 6H), 2.1 (m, 6H), 2.55 (t, 3H), 4.05 (q, 2H), 4.8 (t, 1H), 4.9 (d, 2H), 5.5 (t, 1H), and 5.7 (m, 2H).

Example 25

3-(But-3-en-1-yl)-7,11-dimethyldodeca-2E,6E,10-trien-1-ol (Compound L): Compound K (313 mg. 1.02 mmol) was dissolved in anhydrous toluene (3 mL) and chilled to −78° C. DIBAL-H (3 mL of a 1M soln, 3.0 mmol) was added dropwise. The solution reacted for 1 hour and was warmed slightly. The reaction was quenched with 10% aqueous sodium potassium tartarate. The layers were separated and the aqueous layer was extracted (3×20 mL) with ethyl acetate. The organic layers were combined, washed with brine (10 mL), dried, filtered and concentrated. Purification was performed by flash chromatography (hexane/ethyl acetate 90:10) and gave L in 58% yield (150 mg). $^1H$ NMR (300 MHz, $CDCl_3$): δ 1.1 (t, 3H), 1.45 (s, 3H), 1.55 (s, 3H), 1.9 (m, 6H), 2.1 (m, 6H), 4.3 (d, 2H), 4.8 (t, 1H), 4.9 (d, 2H), 5.6 (t, 1H), and 5.7 (m, 1H).

Example 26

1-Bromo-3-(but-3-methyl-2-en-1-yl)-7,11-dimethyl-dodeca-2Z,6E,10-triene (Compound M): A solution of alcohol C (830 mg, 3.1 mmol), carbon tetrabromide (1.71, 5.8 mmol), and triphenyl phosphine (1.21 g., 3.8 mmol) was made in anhydrous dichloromethane and cooled to 0° C. The mixture was warmed to room temperature over an hour. The solution was concentrated and then resuspended in hexanes and filtered. It was then dried with MgSO₄ and concentrated. The product M was produced in 90% yield (924 mg) and was further elaborated without purification. $^1$H NMR (300 MHz, CDCl₃): δ 1.8 (s, 3H), 2.0 (t, 12H), 2.2-2.3 (m, 8H), 3.1 (d, 2H), 4.3 (d, 2H), 5.4 (m, 3H), and 5.9 (t, 1H).

Example 27

Ethyl 3-oxo-7-(but-3-methyl-2-en-1-yl)-11,15-dimethyl-hexadeca-6Z,10E,14-trienoate (Compound N): Sodium ethyl acetoacetate (1.43 g, 9.4 mmol) was dissolved in anhydrous THF and cooled to 0° C. The dianion was then generated by the dropwise addition of a 2.0 M n-BuLi solution (4.7 mL, 9.4 mmols). The reaction was allowed to proceed for 30 minutes, and then bromide M (900 mg, 2.7 mmol) was added. After 45 minutes the reaction was quenched with 10% aqueous citric acid. The aqueous layer was extracted with ether (3×15 mL). The organic layers were combined, washed with brine (30 mL), dried with MgSO₄, filtered and concentrated. The compound was purified with flash chromatography (hexanes/ethyl acetate 99:1) and gave the product N in 70% yield (725 mg).

Example 28

3-(Trifluoromethylsulfonyl)-7-(but-3-methyl-2-en-1-yl)-11,15-dimethyllhexadeca-2E,6Z,10E,14-tetraene ethyl ester (Compound O): Beta-ketoester N (328 mg, 0.85 mmol) was dissolved in 10 mL THF and cooled to −78° C. Potassium bis(trimethylsilyl)amide (KHMDS, 0.5 M in toluene, 2.05 mL, 1.1 mmol) was added dropwise. After five minutes has elapsed, the 2-[N,N-bis(trifluoromethylsulfonyl)amino]-5-chloropyridine (433 mg, 1.1 mmol) was added. The reaction was warmed to room temperature over 12 hours. The solution is diluted with ether and the reaction was quenched with 10% aqueous citric acid solution. The aqueous layer was extracted with ether (3×15 mL). The organic layers were combined, washed with brine (30 mL), dried with MgSO₄, filtered and concentrated. The crude mixture was purified with flash chromatography (hexanes/ethyl acetate 99:1) to give the triflate O in 58% yield (256 mg). $^1$H NMR (300 MHz, CDCl₃): δ 1.0 (t, 3H), 1.3 (t, 3H), 1.6 (t, 3H), 1.8 (t, 9H), 2.3 (t, 4H), 2.4 (t, 4H), 2.7 (d, 2H), 4.2 (q, 2H), 5.1 (t, 1H), 5.2 (t, 3H), and 5.8 (s, 1H).

Example 29

Ethyl 7-(But-3-methyl-2-en-1-yl)-3,11,15-trimethylhexadeca-2E,6Z,10E,14-tetraenoate (Compound P): Copper (I) cyanide (100 mg, 1.15 mmol) was suspended in ether and chilled to −78° C. Then a solution of methyl magnesium bromide (3.0 M in ether; 0.25 mL, 0.76 mmol) reagent was added and the mixture was warmed to 0° C. for five minutes. The mixture was again chilled to −78° C. and triflate O (200 mg, 0.38 mmol) was added to the reaction slowly. After 90 minutes the reaction was warmed to 0° C. and quenched with 10% aqueous ammonium chloride. The organic layer and the aqueous layers were separated and the aqueous layer was extracted three times with ether. The organic layers were combined dried with magnesium sulfate, filtered and concentrated under reduced pressure. The compound was purified with flash chromatography (hexanes/ethyl acetate 99:1) and gave P in a 95% yield (140 mg). $^1$H NMR (300 MHz, CDCl₃): δ 1.1 (t, 3H), 1.3 (t, 3H), 1.4 (t, 12H), 1.8 (m, 2H), 1.9 (m, 2H), 2.5 (d, 2H), 3.9 (q, 2H), 4.8 (t, 1H), 4.9 (t, 3H), and 5.4 (s, 1H).

Example 30

7-(But-3-methyl-2-en-1-yl)-3,11,15-trimethylhexadeca-2E,6Z,10E,14-tetraen-1-ol (Compound Q): Compound P (200 mg, 0.52 mmol) was dissolved in anhydrous toluene (3 mL) and chilled to −78° C. DIBAL-H (1.48 mL of a 1M solution, 1.48 mmol) was added dropwise. The solution reacted for 1 hour and was warmed slightly. The reaction was quenched with 10% aqueous sodium potassium tartarate. The layers were separated and the aqueous layer was extracted (3×20 mL) with ethyl acetate. The organic layers were combined, washed with brine (10 mL), dried, filtered and concentrated. The reaction mixture was purified with flash chromatography (hexanes/ethyl acetate 90:10) to give alcohol Q in a 41% yield (70 mg). $^1$H NMR (300 MHz, CDCl₃): δ 1.7 (t, 12H), 1.8 (m, 2H), 2.1-2.3 (m, 8H), 2.8 (d, 2H), 4.3 (d, 2H), 5.2 (t, 1H), 5.3 (t, 3H), and 5.7 (t, 1H).

Example 31

Ethyl 7,11,15-Trimethylhexadeca-6E,10E,14-trien-2-ynoate (Compound S): Triflate R, CuI (55.3 mg, 0.29 mmol), Ph₃As (89 mg., 0.29 mmol), and bis(benzonitrile)-palladium (II) chloride (61 mg., 0.16 mmol) were placed in an argon-flushed flask and dissolved in NMP (6 mL). The mixture was immersed in an oil bath maintained at a temperature of 100-105° C., (3-methyl-but-2-en-1-yl)tributyltin (1.54 g, 1.4 mmol) was added, and the reaction mixture was stirred for 12 h. It was then cooled, taken up in ethyl acetate (25 mL), and washed with aqueous KF (2×20 mL) and H₂O (2×20 mL). The aqueous layers were back extracted with ethyl acetate (30 mL) and the combined organic layers were dried (MgSO₄), filtered and concentrated. Purification by flash chromatography (hexane/ethyl acetate 98:2) gave 559 mg of S, in a 61% yield %. $^1$H NMR (300 MHz, CDCl₃): δ 1.3 (t, 3H), 1.6 (s, 9H), 1.7 (s, 3H), 2.0-2.2 (m, 12H), 2.4 (m, 4H), 4.3 (q, 2H), and 5.1-5.2 (m, 3H).

Example 32

7,11,15-Trimethyl-hexadeca-6E,10E,14-trien-2-yn-1-ol (Compound T): Ester S (500 mg, 1.58 mmol) was dissolved in anhydrous toluene (3 mL) and chilled to −78° C. DIBAL-H (625 mg, 4.4 mmol) was added dropwise. The solution reacted for 1 hour and was warmed to 0° C. The reaction was quenched with 10% aqueous sodium potassium tartarate. The layers were separated and the aqueous layer was extracted (3×20 mL) with ethyl acetate. The organic layers were combined, washed with brine (10 mL), dried, filtered and concentrated. Purification by flash chromatography (hexane/ethyl acetate 90:10) gave 150 mg of T, in a 29% yield. The structure of this compound was confirmed by $^1$H and $^{13}$C NMR.

Example 33

Ethyl 3-(3-methyl-2-butenyl)-7-methylocta-2E,6-dienoate (Compound V): Triflate U (1.8.g., 5.41 mmol), CuO (430 mg, 5.4 mmol), Ph₃As (165 mg, 0.54 mmol), and bis (benzonitrile)-palladium (II) chloride (114 mg. 0.29 mmol) were placed in an argon-flushed flask and dissolved in NMP (6 mL). The mixture was immersed in an oil bath maintained at a temperature of 100-105° C., (3-methylbut-2-enyl)tributyltin (8.2 mmol) was added, and the reaction mixture was stirred for 12 h. It was then cooled, taken up in ethyl acetate (25 mL), and washed with aqueous KF (2×20 mL) and H₂O (2×20 mL). The aqueous layers were back extracted with ethyl acetate (30 mL), and the combined organic layers were dried (MgSO₄), filtered, and concentrated. Purification by flash chromatography (hexane/ethyl acetate 98:2) gave V in an 89% yield (1.2 g). $^1$H NMR (300 MHz, CDCl₃): δ 1.4 (t, 12H), 1.7 (m, 4H), 2.7 (t, 3H), 3.35 (d, 2H), 4.2 (q, 2H), 5.3 (t, 2H) and 5.5 (t, 1H).

Example 34

3-(3-Methyl-2-butenyl)-7-methylocta-2E,6-diene-1-ol (Compound W): Compound V (1.2 g, 4.84 mmol) was dissolved in anhydrous toluene (3 mL) and chilled to −78° C. DIBAL-H (1.88 g, 13.55 mmol) was added dropwise. The solution reacted for 1 hour and was warmed slightly. The reaction was quenched with 10% aqueous sodium potassium tartarate. The layers were separated and the aqueous layer was extracted (3×20 mL) with ethyl acetate. The organic layers were combined, washed with brine (10 mL), dried, filtered and concentrated. Purification was performed by flash chromatography (hexane/ethyl acetate 90:10) and gave W in 70% yield (700 mg). The structure of this compound was confirmed by $^1$H NMR.

Example 35

1-Bromo-3-(3-methyl-2-butenyl)-7-methylocta-2E,6-diene (Compound X): A solution of the alcohol W (700 mg, 3.41 mmol), carbon tetrabromide (1.9 g, 5.8 mmol), and triphenyl phosphine (1.42 g, 4.26 mmol) was made in anhydrous dichloromethane (15 mL) and cooled to 0° C. The mixture was warmed to room temperature over an hour. The solution was concentrated and then resuspended in hexanes and filtered. It was then dried with MgSO$_4$ and concentrated. The product X (800 mg, 87% yield) was used directly in the next step without purification. $^1$H NMR (300 MHz, CDCl$_3$): δ 1.5 (t, 12H), 1.7 (m, 4H), 2.9 (d, 2H), 4.0 (d, 2H), 5.1 (m, 3H).

Example 36

Ethyl 3-oxo-7-(3-methyl-2-but-en-yl)-11-methyldodeca-6E,10-dieonoate (Compound Y): Sodium ethyl acetoacetate (1.59 g, 10.45 mmol) was dissolved in anhydrous THF (25 mL) and cooled to 0° C. The dianion was then generated by the dropwise addition of a 2.0 M n-BuLi solution (5.2 mL, 10.45 mmol). The reaction was allowed to proceed for 30 minutes, and then bromide X (800 mg, 2.98 mmol) was added. After 45 minutes the reaction was quenched with 10% aqueous citric acid. The aqueous layer was extracted with ether (3×15 mL). The organic layers were combined, washed with brine (30 mL), dried with MgSO$_4$, filtered and concentrated. The compound was purified by flash chromatography (hexanes/ethyl acetate 99:1) and gave Y in 70% yield (668 mg). $^1$H NMR (300 MHz, CDCl$_3$): δ 1.2 (t, 3H), 1.6 (t, 12H), 2.1 (m, 4H), 2.3 (q, 2H), 2.5 (t, 2H), 2.7 (d, H), 3.35 (s, 2H), 4.1 (q, 2H), and 5.0-5.1 (m, 3H).

Example 37

Ethyl-3-(trifluoromethylsulfonyl)-7-(but-3-methyl-2-en-1-yl)-11-methyldodeca-2E,6E,10-trienoate (Compound Z): β-Ketoester Y (240 mg, 0.75 mmol) was dissolved in 10 mL of THF and cooled to −78° C. Potassium bis(trimethylsilyl) amide (KHMDS; 2 mL of a 0.5 M solution, 098 mmol) was added dropwise. After five minutes has elapsed, 2-[N,N-bis (trifluoromethylsulfonyl)amino]-5-chloropyridine (384 mg, 0.98 mmol) was added as a solid. The reaction was warmed to room temperature over 12 hours. The solution is diluted with ether and the reaction was quenched with 10% aqueous citric acid solution. The aqueous slayer was extracted with ether (3×15 mL). The organic layers were combined, washed with brine (30 mL), dried with MgSO$_4$, filtered, and concentrated. The crude mixture was purified by flash chromatography (hexanes/ethyl acetate 99:1) and gave the triflate Z in 53% yield (180 mg). $^1$H NMR (300 MHz, CDCl$_3$): δ 1.2 (t, 3H), 1.7 (t, 12H), 2.1 (m, 4H), 2.3 (t, 2H), 2.4 (t, 2H), 2.7 (d, 2H), 4.2 (q, 2H), 5.0 (t, 1H), and 5.1 (t, 2H).

Example 38

Ethyl 7-(But-3-methyl-2-en-1-yl)-3,11-dimethyldodeca-2E,6E,10-trienoate (Compound AA): Copper (I) cyanide (104 mg, 1.17 mmol) was suspended in ether and chilled to −78° C. The methyl magnesium bromide (0.25 mL of a 3M solution, 0.78 mmol) reagent was added and the mixture was warmed to 0° C. for five minutes. The mixture was again chilled to −78° C. and triflate Z was added to the reaction slowly as a solution in ether. After 90 minutes the reaction was quenched with 10% aq. ammonium chloride. The organic layer and the aqueous layers were separated and the aqueous layer was extracted three times with ether. The organic layers were combined, dried with magnesium sulfate, filtered and concentrated under reduced pressure. The crude mixture was purified using flash chromatography with 1% ethyl acetate in hexanes and AA was obtained in a 90% yield (105 mg). $^1$H NMR (300 MHz, CDCl$_3$): δ 1.2 (t, 2H), 1.7 (t, 12H), 1.8 (t, 2H), 1.9 (t, 2H), 2.1 (t, 3H), 2.7 (d, 2H), 4.2 (q, 2H), 5.0 (t, 1H), and 5.1 (t, 2H).

Example 39

7-(But-3-methyl-2-en-1-yl)-3,11-dimethyldodeca-2E,6E,10-trien-ol (Compound BB)

Compound AA (165 mg, 0.52 mmol) was dissolved in anhydrous toluene (3 mL) and chilled to −78° C. A 1M solution of DIBAL-H. (1.46 mL, 1.46 mmol) was added dropwise. The solution reacted for 1 hour and was warmed slightly. The reaction was quenched with 10% aqueous sodium potassium tartarate. The layers were separated and the aqueous layer was extracted (3×20 mL) with ethyl acetate. The organic layers were combined, washed with brine (10 mL), dried, filtered and concentrated. Flash column purification (Hexanes/ethyl acetate 90:10) afforded a 55% yield (80 mg) of alcohol BB. $^1$H NMR (300 MHz, CDCl$_3$): δ 1.7 (t, 12H), 1.8 (t, 2H), 1.9 (t, 2H), 2.1 (t, 3H), 2.7 (d, 2H), 4.1 (d, 2H), 5.0 (t, 1H), and 5.1 (t, 2H).

What is claimed is:

1. A compound of the formula

8

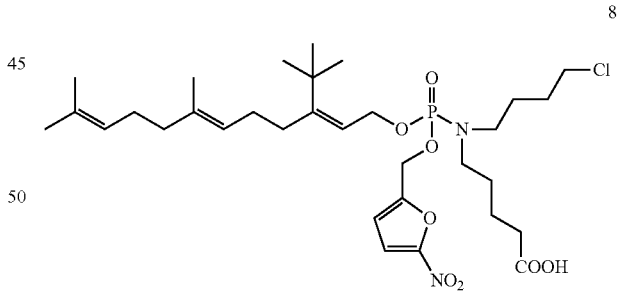

or a pharmaceutically-acceptable salt thereof.

2. A pharmaceutical composition comprising a therapeutically effective amount of the compound, or a pharmaceutically-acceptable salt thereof, of claim 1 and a pharmaceutically acceptable carrier, diluent, or excipient therefor.

* * * * *